US011395802B2

(12) United States Patent
David et al.

(10) Patent No.: US 11,395,802 B2
(45) Date of Patent: Jul. 26, 2022

(54) BIODEGRADABLE POLYMERIC PARTICLES ENCAPSULATING AN ACTIVE AGENT, PHARMACEUTICAL COMPOSITIONS AND USES THEREOF

(71) Applicants: Auburn University, Auburn, AL (US); Altimmune, Inc., Gaithersburg, MD (US)

(72) Inventors: Allan E. David, Auburn, AL (US); Henry J. Baker, Auburn, AL (US); Aime K. Johnson, Auburn, AL (US); M. Scot Roberts, Myersville, MD (US); Kent R. Van Kampen, Payson, UT (US); Prachi Sangle, Auburn, AL (US)

(73) Assignees: Auburn University, Auburn, AL (US); Altimmune, Inc., Gaithersburg, MD (US)

( * ) Notice: Subject to any disclaimer, the term of this patent is extended or adjusted under 35 U.S.C. 154(b) by 274 days.

(21) Appl. No.: 15/706,335

(22) Filed: Sep. 15, 2017

(65) Prior Publication Data
US 2018/0078507 A1    Mar. 22, 2018

Related U.S. Application Data

(60) Provisional application No. 62/395,798, filed on Sep. 16, 2016.

(51) Int. Cl.
| | |
|---|---|
| A61K 9/50 | (2006.01) |
| A61K 9/51 | (2006.01) |
| A61K 39/12 | (2006.01) |
| A61P 31/20 | (2006.01) |
| A61P 31/16 | (2006.01) |
| A61K 9/00 | (2006.01) |
| A61K 9/19 | (2006.01) |
| A61K 39/145 | (2006.01) |
| A61K 39/235 | (2006.01) |
| A61K 39/00 | (2006.01) |

(52) U.S. Cl.
CPC .......... *A61K 9/5036* (2013.01); *A61K 9/0095* (2013.01); *A61K 9/19* (2013.01); *A61K 9/5031* (2013.01); *A61K 9/5153* (2013.01); *A61K 39/12* (2013.01); *A61K 39/145* (2013.01); *A61K 39/235* (2013.01); *A61P 31/16* (2018.01); *A61P 31/20* (2018.01); *A61K 9/0019* (2013.01); *A61K 2039/55555* (2013.01); *C12N 2710/10034* (2013.01); *C12N 2710/10343* (2013.01); *C12N 2760/16034* (2013.01); *C12N 2760/16071* (2013.01); *C12N 2760/16134* (2013.01)

(58) Field of Classification Search
CPC .......................... A61K 9/5161; A61K 9/5153
See application file for complete search history.

(56) References Cited

U.S. PATENT DOCUMENTS

| | | | | |
|---|---|---|---|---|
| 6,080,429 A | * | 6/2000 | Cleland | A61K 9/1647 264/4.1 |
| 8,449,915 B1 | | 5/2013 | Hsing-Wen et al. | |
| 2006/0024377 A1 | * | 2/2006 | Ying | A61K 9/143 424/489 |
| 2014/0171385 A1 | | 6/2014 | Burbank et al. | |
| 2014/0199381 A1 | * | 7/2014 | Ying | A61K 35/15 424/451 |
| 2015/0030655 A1 | | 1/2015 | Jeon et al. | |
| 2015/0165020 A1 | * | 6/2015 | Jaklenec | A61P 31/00 424/206.1 |
| 2015/0297706 A1 | | 10/2015 | Kaltenboeck et al. | |

FOREIGN PATENT DOCUMENTS

| | | |
|---|---|---|
| CN | 102580162 A | 7/2012 |
| WO | 03089022 A1 | 10/2003 |
| WO | 2011026111 A1 | 3/2011 |

(Continued)

OTHER PUBLICATIONS

Sanna, International Journal of Biological Macromolecules, 72, 2015 (Year: 2015).*
McHugh, et al., "Single-injection vaccines: Progress, challenges, and opportunities", J Control Release. 2015;219:596-609. doi: 10.1016/j.jconrel.2015.07.029.
Jaganathan, et al., "Development of a single-dose stabilized poly(D,L-lactic-co-glycolic acid) microspheres-based vaccine against hepatitis B", J Pharm Pharmacol. 2004;56(10):1243-1250. doi:10.1211/0022357044418.
Singh, et al., "Controlled release microparticles as a single dose diphtheria toxoid vaccine immunogenicity in small animal models", Vaccine. 1998;16(4):346-352. doi:10.1016/S0264-410X(97)80912-7.

(Continued)

*Primary Examiner* — Susan T Tran
*Assistant Examiner* — William Craigo
(74) *Attorney, Agent, or Firm* — McKee, Voorhees & Sease PLC

(57) ABSTRACT

Therapeutic or prophylactic compositions providing an active agent, such as an antigen or a vector that contains and expresses an antigen, encapsulated in or incorporated into a biodegradable polymeric particle are provided. The compositions can also provide an active agent that is not encapsulated in or incorporated into the biodegradable polymeric particle in order to provide an initial or prime delivery of the active agent. Particles or composites providing an active agent encapsulated by a first and second polymer are also provided, wherein polymers are distributed in a gradient from a core of the composite to a surface of the composite, and configured to provide a delayed release of the active agent by a period of 7 days to 6 months. Methods of producing composites are also provided. Pharmaceutical formulations providing a single dose composition are also provided, along with methods for administering the pharmaceutical compositions to a subject in need thereof a therapeutically effective amount of an active agent are provided.

19 Claims, 11 Drawing Sheets

(56) References Cited

FOREIGN PATENT DOCUMENTS

| WO | WO-2011138050 A1 | * | 11/2011 | ........... A61K 9/5153 |
|---|---|---|---|---|
| WO | 2014071207 A1 | | 5/2014 | |
| WO | 2015104414 A1 | | 7/2015 | |

OTHER PUBLICATIONS

Zheng, et al., "Alginate-chitosan-PLGA composite microspheres enabling single-shot hepatitis B vaccination", AAPS J. 2010; 12(4):519-524. doi:10.1208/s12248-010-9213-1.

Slütter B, Bal S, Keijzer C, et al. Nasal vaccination with N-trimethyl chitosan and PLGA based nanoparticles Nanoparticle characteristics determine quality and strength of the antibody response in mice against the encapsulated antigen. Vaccine. 2010;28(38):6282-6291. doi:10.1016/j.vaccine.2010.06.121.

Tobio, et al., "A novel system based on a poloxamer/PLGA blend as a tetanus toxoid delivery vehicle", Pharm Res. 1999;16(5):682-688. doi:10.1023/A:1018820507379.

Cleland, et al. "Development of a single-shot subunit vaccine for HIV-I: Part 4. Optimizing microencapsulation and pulsatile release of MN rgp120 from biodegradable microspheres", J Control Release. 1997;47(2):135-150. doi:10.1016/S0168-3659(96)01625-2.

Wang, et al., "PLGA/polymeric liposome for targeted drug and gene co-delivery". Biomaterials. 2010;31 (33):8741-8748. doi:10.1016/j.biomaterials.2010.07.082.

Kamaly, et al., "Degradable Controlled-Release Polymers and Polymeric Nanoparticles: Mechanisms of Controlling Drug Release", Chem Rev. 2016;116(4):2602-2663. doi:10.1021/acs.chemrev.5b00346.

Sanchez, et al., "Pulsed controlled-released system for potential use in vaccine delivery", J Pharm Sci. 1996;85 (6):547-52. doi:10.1021/js960069y.

Jeong, et al., "Doxorubicin release from core-shell type nanoparticles of poly(DL-lactide-co-glycolide)-grafted dextran", Arch Pharm Res. 2006;29(8):712-719. doi:10.1007/BF02968257.

Cleland, J.L., "Design and production of single immunized vaccines using polylactide polycolide systems", pdf. In: Vaccine Design. Springer; 1995:439-462.

Tzeng, et al. "Thermostabilization of inactivated polio vaccine in PLGA-based microspheres for pulsatile release," Journal of Controlled Release 233 (2016): 101-113.

Nie, et al., "PLGA/chitosan composites from a combination of spray drying and supercritical fluid foaming techniques: New carriers for DNA delivery", Journal of Controlled Release, vol. 129, 207-214 (2003).

Akagi, A, Baba, M and Akashi, M. Biodegradable Nanoparticles as vaccine Adjuvants and Delivery Systems Regulation of Immune Responses by Nanoparticle-Based Vaccine. Advances in Polymer Science. 247 (2012) 31-64.

Baxendale, et al., "Single shot tetanus vaccine manufactured by a supercritical fluid encapsulation technology", International Journal of Pharmaceutics.413 (2011) 147-154.

Chua, et al., "Chitosan Microparticles and Nanoparticles as Biocompatible Delivery Vehicles for Peptide and Protein-Based immunocontraceptive Vaccines", Molecular Pharmaceutics 2012, 9, 81-90.

Wang, et al., "Time course study of the antigen-specific immune response to a PLGA microparticle vaccine formulation", Biomaterials, 2014, 35, 8385-8393.

Kim, et al., "Enhancing the therapeutic efficacy of adenovirus in combination with biomaterials", Biomaterials 2012, 33, 1838-1850.

Jiang, et al., "Biodegradable poly (lactic-co-clycolic adid) microparticles for injectable deliver of vaccine antigens", Advanced Drug Delivery Reviews 2005, 57, 391-410.

Galloway, et al., "Development of a nanoparticle-based influenza vaccine using the Print technology", Nanomedicine: Nanotechnology, Biology and Medicine 2013, 9, 523-531.

Lemke, et al., "Antigen-coated poly a-hydroxy acid based microparticles for heterologous prime-boost adenovirus based vaccinations", Biomaterials 2013, 34, 2524-2529.

Whalen, et al., "Microencapsulated vaccines to provide prolonged immunity with a single administration", American Society of Artificial Internal Organs Journal, 1996, (abstract).

Patil, et al., "A review on novel approach pulsatile drug delivery system", Int. J. Pham. Sci. Rev. Res, 2013, 21(1), 209-222.

Caló, et al., "Biomedical Applications of Hydrogels: A Review of Patents and Commercial Products", European Polymer Journal, vol. 65, 252-267 (2015).

Keles, et al., "Investigation of Factors Influencing the Hydrolytic Degradation of Single PLGA Microparticles", Polymer Degradation and Stability, vol. 119, 228-241 (2015).

"The International Search Report and Written Opinion of the International Searching Authority", in connection to PCT/US17/51830, filed Sep. 15, 2017 dated Jan. 17, 2018.

Sonia, T. A., et al., "Chitosan and Its Derivatives for Drug Delivery Perspective", Adv. Polym. Sci. (2011) 243, pp. 23-54. Apr. 8, 2011.

* cited by examiner

BIODEGRADABLE POLYMERIC PARTICLES ENCAPSULATING AN ACTIVE AGENT, PHARMACEUTICAL COMPOSITIONS AND USES THEREOF

CROSS REFERENCE TO RELATED APPLICATIONS

This application claims priority and is related to U.S. Provisional Application Ser. No. 62/395,798 filed on Sep. 16, 2016 and entitled Protecting Animal and Human Health Using Nanotechnology to Enhance Vaccines. The entire contents of this patent application are hereby expressly incorporated herein by reference including, without limitation, the specification, claims, and abstract, as well as any figures, tables, or drawings thereof.

FIELD OF THE INVENTION

The invention relates to therapeutic or prophylactic compositions for inducing an immune response, including single or delayed dosing vaccine compositions. In particular, the compositions provide an active agent, such as an antigen or a vector that contains and expresses an antigen, encapsulated in or incorporated into a biodegradable polymeric particle, including for example nanoparticles, wherein the particle comprises at least a first polymer with a first pH dependent rate of degradation that serves to form a solid matrix to encapsulate the antigen or vector and a second polymer with a second pH dependent rate of degradation that is different from the first rate of degradation, to serve as a binder that modulates overall degradation rate of the particle and induce a prolonged time to boost delivery of the antigen or vector. The compositions can further provide an antigen or a vector that is not encapsulated in or incorporated into the biodegradable polymeric particle to provide an initial or prime delivery of the antigen or vector. Particles or composites providing an active agent encapsulated by a first and second polymer are also provided, wherein polymers are distributed in a gradient from a core of the composite to a surface of the composite, and configured to provide a delayed release of the active agent by a period of 7 days to 6 months. Pharmaceutical formulations employing the single dose compositions are further provided in the invention. In addition, a method for administering the pharmaceutical compositions to a subject in need thereof a therapeutically effective amount of the composition is provided.

BACKGROUND OF THE INVENTION

In the 215 years since Edward Jenner observed that Cow Pox protects people from Small Pox, vaccination (Vacca, Latin for cow) has prevented more human and animal suffering and death than any other single medical procedure. Vaccinology in the 20th century was characterized by refinement of Jenner's principle of protection using less pathogenic organisms with natural or induced reduction of virulence. During the past 20 years, spectacular advances in immunology and the advent of molecular medicine have ushered in exciting new opportunities for vaccine development.

New animal and public health challenges require that advanced molecular methods be employed to improve vaccines that protect our food supply and the health of animals and the public. Exemplary threats and challenges include increasing incidence of antibiotic resistant organisms, reduced dependence on antibiotics for animal production, natural mutations causing "species jumping" of pathogens such as feline and canine parvovirus, newly recognized zoonotic pathogens exemplified by SARS, Prions and Ebola, bio-warfare pathogens such as anthrax or engineered avian influenza and interspecies transmission of influenza. Development of new vaccines using modern molecular technology must be pursued to protect our food supply and the health of companion animals, wild/feral species and the public.

New, powerful vaccine technologies, combined with nanotechnologies, could revolutionize vaccines. For example, non-replicating adenovirus vectors have been engineered to incorporate and express a variety of antigens, and are safe for the host and environment. While older vaccines require complex, costly and time consuming industrial manufacture of antigens, vectored vaccines induce immune protection by directing host cells to express the antigen. In response to newly recognized pathogens, vectored vaccines can be designed, synthesized and expanded rapidly and economically, while reinventing traditional vaccines takes years. Finally, vectors are themselves immunostimulatory without causing inflammation, and they are safe for the patient, operators and the environment. These many advantages of viral vector technology are embodied in the most advanced of vaccine vectors based on human adenovirus variant 5 (Ad5). This vector system has been shown to induce potent humoral and cell-mediated immune responses, has intrinsic adjuvant properties, induces innate immunity, has effective immunological memory, provides a natural presentation of immunogens and has a broad host tropism. Ad5-vectored vaccines have been shown to be adaptable for induction of protective immunity in humans and a large variety of experimental animal species and they do not vary significantly as a function of either the antigen being expressed or the species being immunized. Therefore, the range of pathogens that can be addressed and the host species that can be protected are virtually limitless as long as the molecular antigen is characterized and can be synthesized by recombinant methods. Because Ad5-vectors are non-replicating, they are safe. In spite of these important characteristics and their extensive successful use in humans and experimental animals, this technological opportunity has been underutilized for animal vaccines. A notable exception is a recent development of an Ad5-vectored vaccine for protection of cattle against Foot and Mouth Disease Virus.

Modern vaccine development is increasingly seeking novel adjuvants and delivery systems to boost immunogenicity. With the ability to control size, shape, composition and surface properties, nanotechnology offers tremendous potential in the biomedical field. Use of nanotechnology in vaccinology has grown so rapidly that it has led to coining of the term "nanovaccinology". While much of the development effort has been for cancer treatment, a few prophylactic nanovaccines have been commercialized (e.g. GlaxoSmithKline's Engerix® for hepatitis B, Cervarix® for human papillomavirus, as well as Merck's Recombivax HB® and Gardasil®) while others are in preclinical trials.

Nanovaccines have been synthesized from a variety of materials, including biodegradable polymers such as poly (D,L-lactic-coglycolic acid)(PLGA), polysaccharides such as alginate and chitosan, as well as inorganic materials such as silica and iron oxide. A number of examples of vaccine encapsulation and their release kinetics have been described in literature. Tetanus vaccine, also known as tetanus toxoid (TT), is a vaccine used to prevent tetanus. Five doses are recommended for children, with a sixth given during adolescence. For adults, everyone is immune after 3 doses with boosting every 10 years. A booster may be given within 48 hours of an injury to individuals of uncertain immunity. Higaki and colleagues attempted to reduce this frequency of reimmunization by encapsulating tetanus vaccine in collagen mini-pellets provide an initial burst and then a continuous release up to 14 days (Vaccine 19.23 (2001): 3091-3096). Jaganathan showed that tetanus toxoid vaccine encapsulated in chitosan microspheres exhibited a continuous release up to 35 days (International journal of pharmaceutics 294.1 (2005): 23-32). Alonso and colleagues studied the in vitro release kinetics and in vivo immune response to tetanus toxoid vaccine encapsulated in PLA and PLGA microspheres, with the goal of replacing the multiple injections currently used in tetanus immunization regimen with a single injection of controlled release devices (Pharmaceutical research 10.7 (1993): 945-953). These particles demonstrated pulsatile release of tetanus toxoid over the course of one-month in vitro and evoked neutralizing antibody titers that were comparable to a single injection of alum-adsorbed tetanus toxoid at an equivalent dose 6 months after in vivo administration. A single injection of either PLGA or chitosan microspheres containing tetanus toxoid-stabilizing excipients elicited tetanus toxoid-specific antibody titers in guinea pigs that were comparable or better than those elicited by two bolus injections of alum-adsorbed tetanus toxoid vaccine administered at 0 and 4 weeks (International Journal of Pharmaceutics 294.1 (2005):23-32). Tobio et al. showed a burst of tetanus toxoid vaccine encapsulated in PLGA microspheres with gelatin/poloxamer core lasting up to 48 hours (Vaccine 18.7 (1999): 618-622). Katare and Panda showed in rats an initial burst followed by continuous release of tetanus toxoid vaccine encapsulated in PLA microspheres for 120 days (European journal of pharmaceutical sciences 28.3 (2006): 179-188).

In guinea pigs, a continuous release for 42 days of Hepatitis B surface antigen encapsulated in PLGA microspheres was achieved (Journal of pharmacy and pharmacology 56.10 (2004): 1243-1250). Similar studies were presented with Hepatitis B surface antigen encapsulated in PLGA (29, 34 and 35) which showed burst release followed by continuous release up to 60 days. Hepatitis B surface antigen was encapsulated in alginate-chitosan-PLGA microsphere which gave 71% continuous release in 2 months; but they observed inflammation at the injection site (AAPS journal 12.4 (2010): 519-524). Those alginate-chitosan-PLGA microspheres were synthesized in a two-step preparation resulting in a protein friendly core microenvironment created by the hydrophilic alginate-chitosan cores that was coated with PLGA. There are still further examples of vaccines encapsulated in PLGA, blending of polymers for vaccine delivery, use of polymer implants to achieve controlled drug release over a period of a few months, and other uses of polymers to modulate degradation kinetics and release kinetics of encapsulated vaccines. However, there remains a clinical need for vaccine compositions providing a single dosage or administration having controlled release of an antigen or viral vector.

Accordingly, it is an objective of the invention to provide a single dose composition to eliminate the need for reimmunization as required for traditional vaccines to achieve full and sustained protection.

It is an objective of the invention to provide a vaccine composition that employs particles to release a vaccine at predetermined intervals after a single injection that mimics the effect of reimmunization and sustains the durability of protection.

It is a further objective of the invention to provide a therapeutic or prophylactic composition, including vaccine compositions employing encapsulation to produce enhanced immune response or enhanced immunogenicity by protecting vaccines from host degradation and permitting targeting of specific immune mediating cells.

A further object of the invention is to overcome conventional limitations of vaccines, including improving immune response to weak antigens, expanding the number and types of diseases conquered, improving methods of vaccination and reducing the cost of vaccination.

A still further object of the invention and methods of employing the same are to limit the need to handle wild animals, feral animals and grazing range herds. In addition, an object of the invention is to avoid the need for boosters and reimmunization eliminating vaccine failures caused by non-compliance with vaccines that require repeated immunizations, and reducing dependence on cold storage to maintain biopotency of vaccine compositions.

Other objects, advantages and features of the present invention will become apparent from the following specification taken in conjunction with the accompanying drawings.

BRIEF SUMMARY OF THE INVENTION

An advantage of the invention is that a single composition, including both therapeutic or prophylactic compositions, can be formulated and dosed to a subject in need thereof to provide both a burst and programmed release of an antigen or vector, from particles to provide both a primary and boost immune response.

In an embodiment, the present invention provides a pharmaceutical composition comprising: a) a biodegradable polymeric composite particle comprising: at least one active agent encapsulated in a hollow or aqueous core by a shell comprising a mixture of a first polymer, wherein the first polymer is a hydrophobic polymer, and a second polymer, wherein the at least one active agent is releaved over a period of 7 days to 6 months; and b) at least one active agent free from and not encapsulated by the polymeric composite particle; wherein the at least one additional active agent provides an initial dose and the polymeric composite particle provides a delayed dose of the active agent, wherein the active agent encapsulated in the core and the active agent free from the particle can be the same active agent or different active agents.

In a further embodiment, the present invention provides a method for delivering an initial dose and a delayed dose in a single administration dose, comprising: administering the pharmaceutical compositions described herein.

In a still further embodiment, the present invention provides methods of producing a particle, comprising: dissolving a first polymer in an organic solvent to generate a solution of the first polymer; generating an oil-in-water emulsion containing the first polymer; combining the emulsion with a solution comprising a second polymer to generate a second emulsion comprising the first and second polymers; and evaporating the organic solvent to harden the emulsion into a solid particle.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 3A shows a vaccine and polymer combined; FIG. 3B shows a vaccine encapsulated in polymers; FIG. 3C shows a vaccine encapsulated in polymers in combination with a catalyst; and FIG. 3D shows a multilayer encapsulation of vaccines employing polymers.

FIG. 4A shows the structure of chitosan, a naturally occurring cationic, biocompatible hydrophilic polymer with a distinctive primary amine group. FIG. 4B shows the structure of poly-lactic glycolic acid (PLGA) is a synthetic, anionic, biodegradable hydrophobic polymer.

FIGS. 6C and 6D show magnified views of FIGS. 6A and 6B, respectively. FIGS. 6A and 6C are of particles encapsulating adenovirus with PLGA and chitosan mixed together. FIGS. 6B and 6D are of particles encapsulating adenovirus where the PLGA formed a central core prior to addition of chitosan; the shell structure is outline in two particles for easy of visualization.

FIGS. 9A-9B show an exemplary synthesis of the composite materials employed in Example 5, wherein FIG. 9A shows the formation of water in oil in water emulsion, and FIG. 9B shows the formation of the composite particles as they are hardened.

FIG. 10A shows size distribution and FIG. 10B shows zeta potential.

FIGS. 11A-11B show PLGA-Chitosan composite synthesis using fluorescently tagged chitosan to demonstrate chitosan distribution in composite particles. The fluorescently tagged chitosan is shown in dark shading (green fluorescence) within the particle, wherein FIG. 11A shows coating containing a greater density of chitosan to provide a sharper burst release, wherein as FIG. 11B has a greater density of chitosan in the core of the particle.

Figure 1:
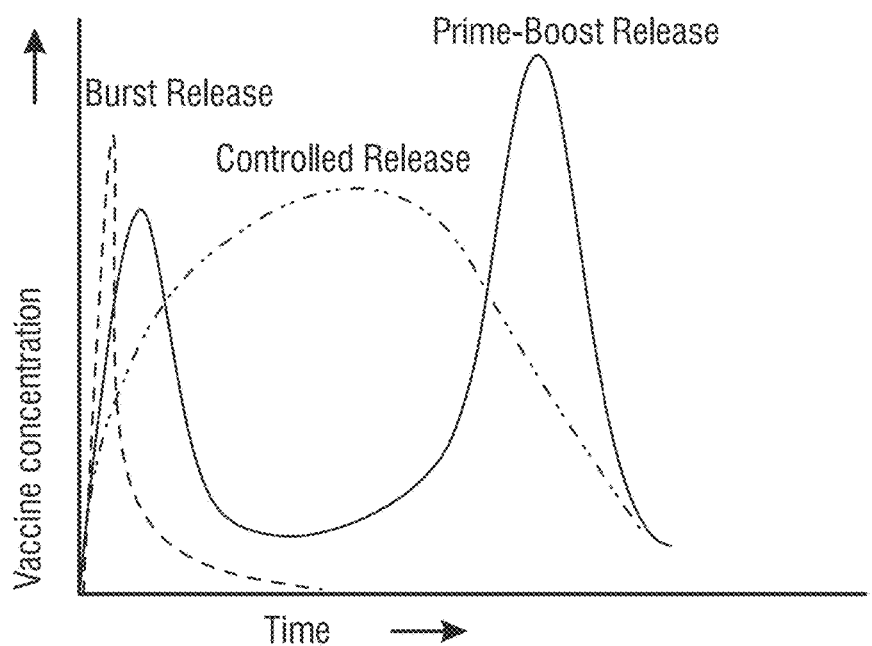
FIG. 1 illustrates burst and programmed release of vaccine after a desired amount of time (shown as a prime-boost release) from particles to achieve a primary and boost immune response according to embodiments of the invention. The burst and prime-boost release are shown in comparison to a conventional controlled release delivery which would have ongoing release of an antigen or vector of the vaccine, which would not be desired in order to avoid inducement of tolerance.

Various embodiments of the present invention will be described in detail with reference to the drawings, wherein like reference numerals represent like parts throughout the several views. Reference to various embodiments does not limit the scope of the invention. Figures represented herein are not limitations to the various embodiments according to the invention and are presented for exemplary illustration of the invention.

DETAILED DESCRIPTION OF THE INVENTION

Introduction

Provided herein are methods, biodegradable composite particles, and pharmaceutical compositions for delivering an active agent, such as an antigen or vector, to an animal in need thereof, wherein delivery is a delayed release of the active agent during a period of about 7 days to about 6 months. The delayed release may be as a single bolus dose, multiple bolus doses over the delayed period or as a sustained release. In embodiments, the biodegradable composite particles comprise at least a first polymer and a second polymer and an active agent that is encapsulated by the polymers, wherein those polymers have various properties that may be fine-tuned to provide for a delayed release at a specified time period. In embodiments, the degradation rate of the first polymer is different than the degradation rate of the second polymer at neutral or physiological pH. Degradation of the polymers may be by hydrolysis, oxidation, enzymatic or catalytic activity, wherein the degradation is determined by the polymer and the linkages or bonds within the polymers. In embodiments, the second polymer is configured to provide a delayed release of the active agent by a period of about 7 days to about 6 months.

The present biodegradable composite particles may comprise a distinct core/shell configuration wherein the active agent is concentrated in the core and a first polymer is concentrated in the core and the second polymer concentrated in the shell, or a homogenous mixture of at least a first and second polymer with the active agent is incorporated throughout the particle, or the core may be hollow or filled with an aqueous solution comprising the active agent encapsulated by a mixture of the first and second polymer. In certain embodiments, the biodegradable composite particles comprise a first and second polymer that exist in a gradient from the core to the surface. In certain other embodiments, the biodegradable composite particles comprise a first and second polymer that exist in a gradient wherein the core is hollow or filled with an aqueous solution and the gradient is in the shell layer surrounding the core. In certain embodiments, at least one of the first or second polymers is a hydrophobic polymer. In embodiments, the first polymer is a hydrophobic polymer and the second polymer is a hydrophilic polymer. In other embodiments, the core is hydrophobic and the shell/coat/surface is hydrophilic.

In embodiments, provided herein are biodegradable polymeric composite particles comprising an active agent encapsulated by a first and second polymer wherein the first and second polymer are distributed in a gradient from a core, or an outer edge of the core, of the composite to a surface of the composite with the first polymer has a higher concentration in the core than the surface and the second polymer has a higher concentration at the surface than the core wherein the first polymer binds the second polymer via hydrogen bonding, and wherein the second polymer is configured to provide a delayed release of the active agent by a period of 7 days to 6 months. In certain embodiments, provided herein are biodegradable polymeric composite particles comprising an active agent encapsulated in a core by a first polymer wherein the first polymer is a hydrophobic polymer and a shell comprising a second polymer, wherein the shell is configured to provide a delayed release of the active agent by a period of 7 days to 6 months. In certain other embodiments, provided herein are biodegradable polymeric composite particles comprising an active agent encapsulated in a hollow or aqueous filed core by a shell comprising a homogenous mixture of a first polymer, wherein the first polymer is a hydrophobic polymer, and a second polymer, wherein the shell is configured to provide a delayed release of the active agent by a period of 7 days to 6 months.

In certain embodiments are provided pharmaceutical compositions that comprise the biodegradable composite particles for administration to an animal in need thereof to provide a delayed release of the active agent comprised within the particle. In other embodiments, the pharmaceutical compositions comprise the biodegradable composite particles and an active agent that is not encapsulated or otherwise stabilized by polymers. In that instance, that pharmaceutical composition provides a single administration dose that provides an initial dose, such as vaccine prime dose, and a delayed dose, such as a vaccine boost dose.

The present invention further provides methods for delivering at least a first and second dose of an active agent in a single administration dose, wherein the method comprises administering a pharmaceutical composition to an animal in need thereof comprising a) the present biodegradable composite particles encapsulating or incorporating an active agent; and, b) an active agent that is not encapsulate or stabilized by a polymer. The active agent that is not encapsulated in the first dose and the active agent encapsulated by the present biodegradable composite particles is the second dose that is delivered via degradation of the composite particle during a time period of 7 days to 6 months after administration of the pharmaceutical composition. In certain embodiments, the biodegradable polymeric composite particles are engineered to provide multiple delayed doses. For example, a particle may comprise one or more shell configurations that each comprise the active agent and degrade releasing the delayed dose(s). In certain embodiments, the pharmaceutical composition provides at least a second delayed dose, at least a third delayed dose, at least a fourth delayed dose, at least a fifth delayed dose, at least a sixth delayed dose, etc. In alternative embodiments, the pharmaceutical composition comprises a first set of biodegradable polymeric composite particles with a first rate of degradation and at least a second set of biodegradable polymeric composite particles with a second rate of degradation that is different from the first degradation rate.

Definitions

The embodiments of this invention are not limited to particular compositions, formulations and methods of employing the same, which can vary and are understood by skilled artisans. It is further to be understood that all terminology used herein is for the purpose of describing particular embodiments only, and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form. Numeric ranges recited within the specification are inclusive of the numbers defining the range and include each integer within the defined range.

Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present invention, the following terminology will be used in accordance with the definitions set out below.

The term "about," as used herein, refers to variation in the numerical quantity that can occur, for example, through typical measuring and liquid handling procedures used for making concentrates or use solutions in the real world; through inadvertent error in these procedures; through differences in the manufacture, source, or purity of the ingredients used to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

The term "animal" refers to mammalian subjects, including humans, horses, dogs, cats, pigs, livestock, and any other mammal, along with birds. As referred to herein the term "animal" also includes an individual animal in all stages of development, including newborn, embryonic and fetal stages.

The term "composite" refers to a combination of at least two polymers comprising a particle that can be on the nanometer scale or exceed the nanometer scale, including for example measurements of the diameter of the particles that are from about 10 nanometers (nm) to about 100 micrometers (micron or µm), about 10 nm to about 75 µm, about 10 nm to about 50 µm, about 10 nm to about 25 µm, about 10 nm to about 10 µm, about 10 nm to about 5 µm, about 10 nm to about 1000 nm, about 20 nm to about 1000 nm, about 50 nm to about 1000 nm, about 100 nm to about 1000 nm, about 100 nm to about 750 nm, about 100 nm to about 500 nm, about 500 nm to about 1000 nm, about 500 nm to about 100 µm, about 500 nm to about 10 µm, about 1 µm to about 100 µm, about 1 µm to about 50 µm, about 5 µm to about 50 µm, about 5 µm to about 25 µm, or about 5 µm to about 10 µm, including all ranges therebetween. As referred to herein, the measurement of the size of a particle or composite can be obtained by dynamic light scattering or electron microscopy.

The term "particle" as used herein, can further include or refer synonymously to "polymeric particles," and can include nanoparticles or a microparticle (or larger if necessary) based upon the measured size of the particle. Further, as one skilled in the art will appreciate based upon the disclosure contained herein, the optimum size of a particle is dependent upon requirements of a specific application, as an increased size can be utilized to provide an increased loading/particle or to increase release time thereof.

The terms "protein," "polypeptide," and "peptide" may be referred to interchangeably herein. However, the terms may be distinguished as follows. A "protein" typically refers to the end product of transcription, translation, and post-translation modifications in a cell. A "peptide", in contrast to a "polypeptide", typically is a short polymer of amino acids, of a length typically of 20 or less amino acids.

The term "weight percent," "wt-%," "percent by weight," "% by weight," and variations thereof, as used herein, refer to the concentration of a substance as the weight of that substance divided by the total weight of the composition and multiplied by 100. It is understood that, as used here, "percent," "%," and the like are intended to be synonymous with "weight percent," "wt-%," etc.

The compositions, formulations and methods of the present invention may comprise, consist essentially of, or consist of the components and ingredients of the present invention as well as other ingredients described herein. As used herein, "consisting essentially of" means that the compositions, formulations and methods may include additional steps, components or ingredients, but only if the additional steps, components or ingredients do not materially alter the basic and novel characteristics of the claimed compositions, formulations and methods.

It should also be noted that, as used in this specification and the appended claims, the term "configured" describes a system, apparatus, or other structure that is constructed or configured to perform a particular task or adopt a particular configuration. The term "configured" can be used interchangeably with other similar phrases such as arranged and configured, constructed and arranged, adapted and configured, adapted, constructed, manufactured and arranged, and the like.

Compositions

Figure 2:
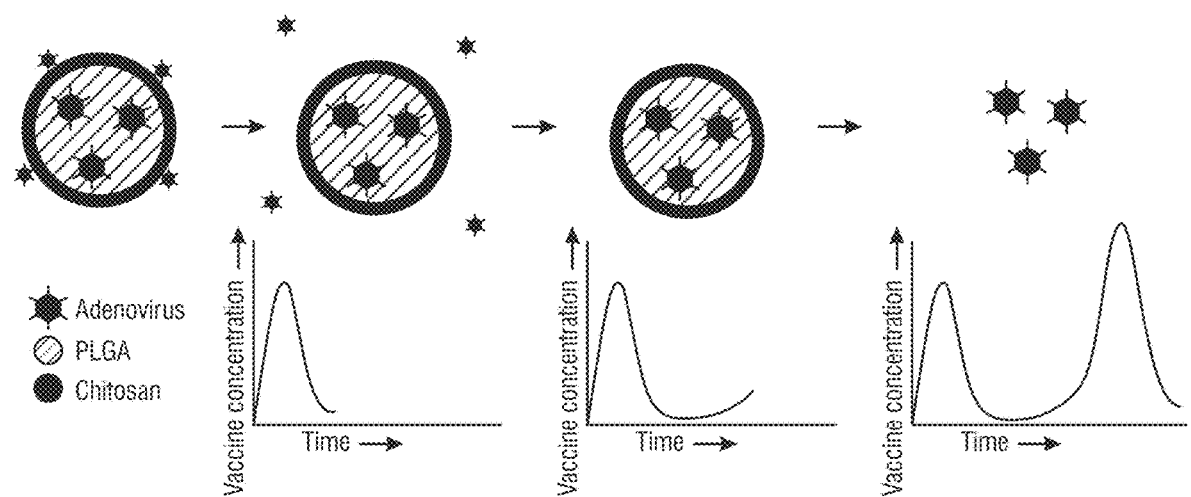
FIG. 2 shows an exemplary release profile of a vaccine from exemplary composite polymers according to embodiments of the invention, wherein the vaccine adsorbed on the surface provides an initial prime dose. Over a period of time, as the first polymer (such as PLGA) undergoes bulk erosion in the composite by hydrolysis, the shell of the second polymer (e.g. chitosan) protects the encapsulated vaccine from a sustained release and instead provides a burst release once the shell degrades sufficiently.

In an aspect, the compositions, formulations and methods of the invention provide a desired burst and programmed release of an active agent (including for example an antigen or vector) from particles, including for example biodegradable polymeric particles to encapsulate and/or incorporate the active agent of the single dose compositions. In an aspect, the single dose compositions can be either therapeutic or prophylactic compositions. FIG. 1 depicts an exemplary burst and programmed release of a vaccine from microcapsules to achieve a primary and boost immune response that eliminates the need for multiple administrations of vaccines and achieves the desired sustained protection and maximum immunogenicity. This is further depicted in FIG. 2, wherein an exemplary release profile of a vaccine from composite polymers according to embodiments of the invention are shown. The depicted virus (adenovirus) is encapsulated with a first polymer PLGA and a second polymer chitosan, wherein the vaccine adsorbed on the surface or in free solution provides an initial prime dose. Thereafter, over a period of time, the PLGA undergoes bulk erosion in the composite by hydrolysis while the chitosan attenuates the hydrolysis by enhancing mechanical integrity and protects the encapsulated vaccine from a sustained release. Instead, a burst release is provided once the shell degrades sufficiently.

Figures 3A, 3B, 3C, 3D:
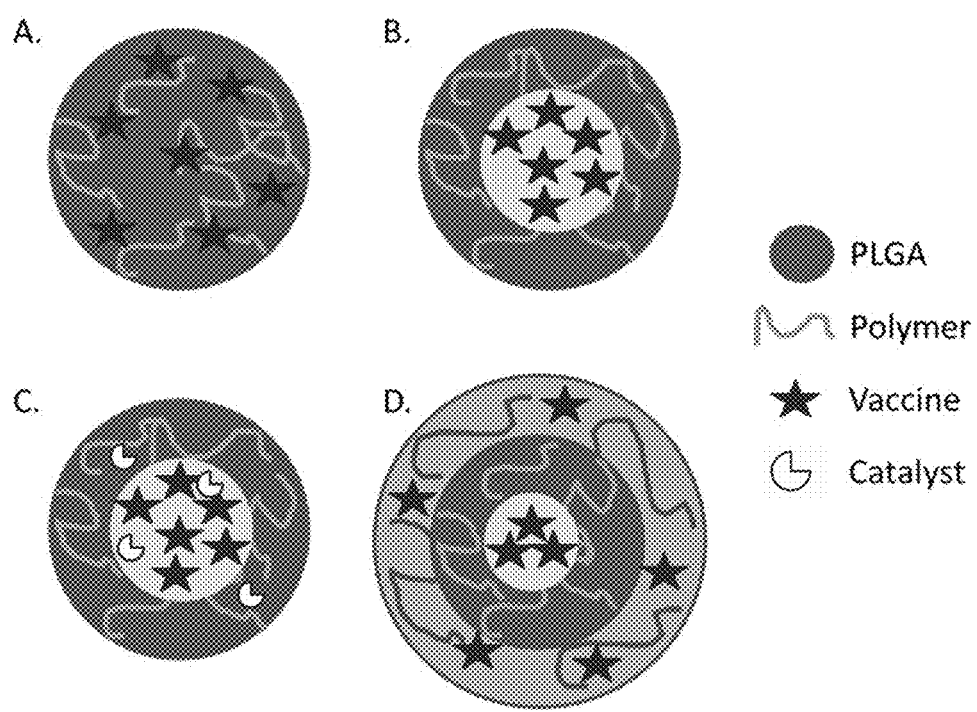
FIGS. 3A-3D illustrate various mechanisms for encapsulation of a vaccine in polymers or combinations of these polymers (composites) to achieve optimal protection and release of vaccines.

FIGS. 3A-3D further illustrate various exemplary embodiments of the single dose compositions for inducing an immune response through the use of particle polymers to deliver a vaccine. In an exemplary and non-limiting depiction, an exemplary vaccine can be an adenovirus vectored vaccine, encapsulated in various mechanisms using polymers, such as poly-lactic glycolic acid (PLGA) or Chitosan, or some combination (e.g. composites) of these polymers. In an aspect as shown in FIG. 3A, a vaccine and polymers can be combined. In an aspect as shown in FIG. 3B, a vaccine can be encapsulated in polymers. In an aspect as shown in FIG. 3C, a vaccine can be encapsulated in polymers in combination with a catalyst. In an aspect as shown in FIG. 3D, a vaccine can be delivered through a multilayer encapsulation with the polymers.

Particles—Composites

In an aspect, the compositions, formulations and methods employ particles, including biodegradable polymeric particles to encapsulate and/or incorporate the active agent of the delayed dose compositions. We have found that using at least one hydrophobic polymer provides for a particle with water content of less than 50%. In embodiments, the hydrophobic polymer is present at a higher percentage (wt-%) than a hydrophilic polymer. These particles are more "solid" than those that comprise a gel. As used herein a "gel" refers to a polymer composition that contains greater than 50% water; a substantially dilute cross-linked system, which exhibits no flow when in the steady-state and by weight, is mostly liquid (e.g. greater than 50%). In embodiments, the present biodegradable polymeric composite particles do not comprise a gel, including hydrogels. In embodiments, the present solid composite particles, excluding an aqueous core if present in the composite particles, contain less than 10% water (w/v), or less than 5% or less than 1% (w/v). In certain embodiments, the solid composite particles contain about 1% water, about 2% water, about 3% water, about 4% water, about 5% water, about 6% water, about 7% water, about 8% water, or about 9% water (w/v). In certain embodiments, the solid composite particles contain about 1% to about 10%, about 2% to about 10%, about 3% to about 10%, about 4% to about 10%, about 5% to about 10% or about 6% to about 10% water (w/v). In certain embodiments, the solid composite particles contain about 1% to about 9%, about 1% to about 8%, about 1% to about 7%, about 1% to about 6%, about 1% to about 5% or about 1% to about 4% water (w/v).

In certain other embodiments, the present biodegradable solid composite particles do not contain greater than 50% water (w/v) in the solid composite particle, excluding an aqueous core if present. In certain embodiments, the present biodegradable solid composite particles do not comprise about 50% to about 99% water (w/v), or about 75% to about 99%, or about 80 to about 99%, or about 85% to about 99%, or about 90% to about 99% water (w/v). As referred to herein the w/v measurement of the water content of the solid composite particles is based on a pre-reconstitution measurement such that the lyophilized composition has not been exposed to water content for hydrolysis to begin degradation of the composite.

In certain embodiments, the present biodegradable composite particles do not comprise alginate polymers (or derivatives thereof), bi-valent or trivalent cations as cross-linking reagents. Alginates form thermally stable gels after binding with a suitable cation, and will form strong stable gels upon binding bi-valent or tri-valent cations. In certain embodiments, the present biodegradable composite particles do not comprise di-valent cations such as $Ca^{2+}$, $Sr^{2+}$, $Zn^{2+}$, $Co^{2+}$ or $Ba^{2+}$. In other embodiments, the present biodegradable composite particles do not comprise tri-valent cations such as $Fe^{3+}$ or $Al^{3+}$.

In embodiments, the hydrophobic polymer may be mixed with at least one hydrophilic polymer, wherein the polymers bind via hydrogen bonding forming a mesh of polymers that may be homogenous or form a gradient of the first and second polymer. The active agent is stabilized in the solid particles wherein degradation, which can be controlled and fine-tuned by the properties of the polymers, delivers a delayed release.

As referred to herein, particles (including nanoparticle technology) beneficially provide advantages to antigens and vector technologies and other active agents, including for example viral vectors. In a first beneficial aspect, the particles and/or composites protect the active agent (e.g. antigen or vector of a vaccine) from host degradation. In a second beneficial aspect, the particles and/or composites allow the active agent (e.g. antigen or vector of a vaccine) to target specific immune mediating cell populations and release vaccines at predetermined intervals to enhance immunogenicity and the durability of protection. In a third beneficial aspect, the particles and/or composites provide a biodegradable system that is safe, effective and acceptable to regulatory agencies for human and animal use.

In an aspect, polymeric particles and/or composites including a combination of at least two polymers encapsulate an active agent to provide delayed release as the polymers degrade. In a further aspect, solid particles and/or composites can be used to attach an active agent to the particle's surface.

The particles and particle technology provide various benefits, including for example, protecting the antigen or vector of a vaccine from host degradation, allowing the antigen or vector of a vaccine to target specific immune mediating cell populations and release vaccines at predetermined intervals to enhance immunogenicity and the durability of protection, as well as provide a biodegradable system that is safe, effective and acceptable to regulatory agencies for human and animal use. In such aspects, the polymers include a combination of at least two polymers to encapsulate an active agent and provide delayed release as the polymers degrade.

In some embodiments, an active agent can be adsorbed on the surface of a particle or composite or in free solution and not adsorbed to the particle or composite. In embodiments, the first and second polymer may be selected from polymers that are naturally occurring or synthetic, those that are hydrophobic or hydrophilic and those with a different degradation rate, at neutral pH, from the other polymer(s) used to form the present biodegradable composite particles. In certain embodiments, a first polymer is a hydrophobic polymer. The term "hydrophobic" as used herein is generally understood to be a polymer that has a limited affinity for water and does not mix well with water. For example, hydrophobic polymers may be non-polar and will aggregate in an aqueous solution and exclude water molecules. The exclusion of water maximizes the hydrogen bonding of the hydrophobic polymer, either to other hydrophobic polymers, a hydrophilic polymer or possibly even the active agent. The hydrogen bonding of the present biodegradable composite particles provides a dense particle that protects the active agent until degradation at an engineered time. In embodiments, hydrophobic polymers include for example, non-polar polymers, polyester polymers, PLGA, PLA, polycaprolactone, and polyanhydrides with hydrophobic co-monomer (e.g. carboxyphenoxypropane). In certain embodiments, the hydrophobic polymer is concentrated in the core of the present composite particles providing a hydrophobic core than encapsulates the active agent. In alternative embodiments, the hydrophobic polymer is mixed throughout the particle, either homogenously with the second polymer and active agent or as a heterogenous mixture.

In certain other embodiments, the second polymer is selected from hydrophilic polymers. As used herein, the term "hydrophilic" is understood to be a polymer that has a strong affinity for water and may be readily soluble in water. For example, hydrophilic polymers may be polar and their interaction with water (and other polar) substances are more thermodynamically favorable than interactions with hydrophobic polymers or substances. In embodiments, hydrophilic polymers include for example, polar polymers, polysaccharides including alginate and chitosan, hydrophilic polyanhydrides, proteins, DNA, and polyvinyl alcohol. In certain embodiments, the hydrophilic polymer is concentrated near the surface or shell/coating, as compared to the core, of the present composite particles providing a hydrophilic surface than encapsulates the active agent. The active agent may be encapsulated or incorporated primarily within the core, primarily on or near the surface, primarily throughout the particle, or primarily within a shell/coating layer. In certain embodiments, the active agent is further attached to or adsorbed to the surface of the particle.

In alternative embodiments, polymers may be selected, either as a first or second polymer, that comprises both hydrophilic and hydrophobic moieties or domains. These polymers may be "amphiphilic". The selected first and second polymers of the present biodegradable composite particles are biodegradable at neutral or physiological pH by hydrolysis, oxidation, via enzymatic or catalytic cleavage, or a combination thereof.

Figure 4A:
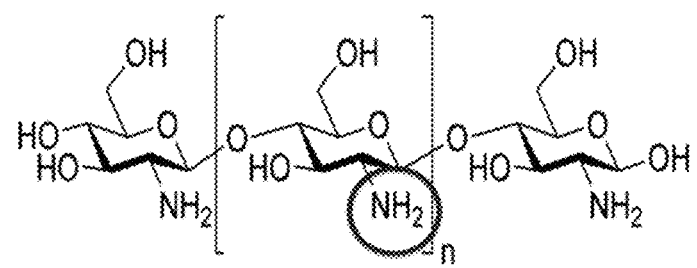
FIGS. 4A-4B illustrates two examples of polymers that can be used to encapsulate vaccines.

Polymers referred to herein can be divided broadly as naturally occurring or synthetic polymers. While many natural polymers suffer batch-to-batch variability, they are attractive because of their relatively low cost and demonstrated bioactivity. In an aspect, suitable polymers are naturally-occurring. An exemplary naturally-occurring polymer is chitosan, a cationic, biocompatible hydrophilic polymer with a distinctive primary amine group (as shown in FIG. 4A). Chitosan is a particularly attractive material due to its biocompatibility, biodegradation, and potential adjuvancy properties. Alginate particles are further examples of naturally-occurring polymers and have been studied for parenteral, mucosal, topical, ocular, intranasal, or any other route of administration. In certain embodiments, the present biodegradable polymeric composite particles do not comprise alginate polymers. In certain other embodiments, the present biodegradable polymeric composite particles may comprise alginate polymers in combination with a hydrophobic polymer wherein the alginate is on or near the surface and the hydrophobic polymer forms a hydrophobic core.

Figure 4B:
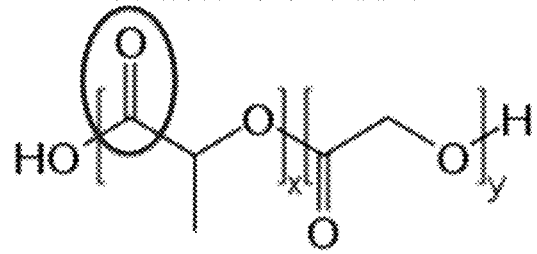

In an aspect, suitable polymers are synthetic. Some examples of synthetic polymers are polyesters like poly lactic acid (PLA), poly glycolic acid (PGA), poly-lactic-glycolic acid (PLGA), polyanhydrides, polyamides, polyurethanes, and the like. An exemplary synthetic polymer is poly-lactic glycolic acid (PLGA), an anionic, biodegradable hydrophobic polymer (as shown in FIG. 4B). Among all polymers, PLGA is among the most commonly used for preparing polymeric particles. In an aspect of the invention, the polymer is PLGA and the composite includes a PLGA polymer. In such an aspect, the molar ratio of glycolic and lactic acids in the polymer chain is about 1:1. However, as one skilled in the art will ascertain, a molar ratio of glycolic acid to lactic acid can vary from 1:0 to 0:1.

In an aspect, the solvent evaporation method is used for the synthesis of composite particles comprising PLGA. In an exemplary aspect, PLGA is dissolved in a volatile, water immiscible organic solvent (e.g. dichloromethane), which is stirred into an aqueous phase to create an oil-in-water emulsion, such as with poly vinyl alcohol. The mixing or stirring of the particles can be for a few minutes to a few hours, or in a preferred aspect from about 2 hours to about 5 hours. Beneficially, the stirring permits the volatile solvent to evaporate and result in the hardened particles. In an embodiment, the water-to-oil ratio of the PLGA mixture is at least about 10:1, at least about 15:1, or preferably at least about 20:1. The volatile solvent is then extracted by evaporation to harden the droplets. The mixture can be sonicated to first create an emulsion before evaporation of the volatile solvent and hardening of the particles. The particles thus obtained are then washed by filtration or centrifugation, and then dried or lyophilized until further use. Single or double emulsion processes are used to encapsulate variety of vaccines, including for example an antigen or vector, in the particles. Beneficially, this polymer preparation technique can produce spherical, porous or hollow microparticles, due to variations in the solvent evaporation rate. Control of the solvent evaporation rate also controls particle morphology and release kinetics. Degradation of the PLGA polymer occurs through hydrolysis of the backbone ester linkage into oligomers and then to monomers. The bulk erosion rate of the polymer, which determines the release profile of any encapsulated agent, is a function of the molar ratio of glycolic and lactic acids in the polymer chain, molecular weight, degree of crystallinity and the glass transition temperature (Tg) of the polymer.

Both naturally-occurring and synthetic polymers used for the nanoparticulate formulations described herein release a portion of a vaccine at the initial administration, with the remaining portion released at predetermined intervals depending on specific chemical engineering of the formulation. Controlled release of vector at predetermined timepoints simulates both priming and boosting making it possible to design single-dose formulations which are minimally invasive and applicable to field use. Mixing formulations that release a vaccine at different intervals allows multiple boosting of the immune response to enhance and prolong immunostimulation. Moreover, incorporation of a vaccine within particles preserves activity by protection against host body degradation. Additionally, a lyophilized form can be stored at ambient conditions and suspended in water before injection, eliminating the need to maintain cold storage to preserve potency. An important additional feature of particles is that they can be modified to target specific antigen presenting cells such as dendritic cells to enhance an immune response.

Without being limited to a particular mechanism of action, the combination of polymers to provide a composite material provides enhanced compositions and formulations for vaccine delivery, including for example an antigen or vector. Accordingly, in an aspect, particle material includes at least a first polymer, with a first rate of degradation that serves to form a solid matrix to encapsulate the antigen or vector, and a second polymer, with a second rate of degradation that is different from the first rate of degradation to serve as a binder that modulates overall degradation rate of the particle and induces a prolonged time to boost delivery. In an exemplary aspect of the invention, the polymers include at least two of the following: poly (L-glycolic acid) (PLGA), chitosan, polyglycolic acid (PGA), polylactic acid (PLA), poly(L-lactic acid) (PLLA), polyglycolide, poly-L-lactide, poly-D-lactide, poly(amino acids), polydioxanone, polycaprolactone, polygluconate, polylactic acid-polyethylene oxide copolymers, polyorthoesters, polyhydroxybutyrate, polyanhydride, polyphosphoester, poly(alpha-hydroxy acid), chitosan, alginate, collagen, dextran, gelatin, cellulose, carboxymethyl cellulose, hydroxypropyl cellulose, modified cellulose, collagen, cellulose acetate, lignin, starch or combinations thereof.

In an exemplary aspect of the invention, a first polymer can include a synthetic polymer, including for example poly (L-glycolic acid) (PLGA), chitosan, polyglycolic acid (PGA), polylactic acid (PLA), poly(L-lactic acid) (PLLA), polyglycolide, poly-L-lactide, poly-D-lactide, poly(amino acids), polydioxanone, polycaprolactone, polygluconate, polylactic acid-polyethylene oxide copolymers, polyorthoesters, polyhydroxybutyrate, polyanhydride, polyphosphoester, poly(alpha-hydroxy acid) or combinations thereof. In such an exemplary aspect, a second polymer can include chitosan, alginate, collagen, dextran, gelatin, cellulose, carboxymethyl cellulose, modified cellulose, collagen, hydroxypropyl cellulose, cellulose acetate, lignin, starch or combinations thereof.

In an aspect, the synthesis of the composite and/or composite material including a first and second polymer includes the dissolving of the polymers into solvents and thereafter mixed together at a volume ratio of about 1:1, or about 0.1:1 to about 1:0.1, including a ranges disclosed therebetween. The volume ratio and also the molar ratio of the polymers employed in the composite and/or composites described herein can be modified based on the desired degradation rate for delivery of the antigen or vector contained therein. As demonstrated in the Examples, change in molar ratio of two exemplary polymers, PLGA and chitosan, did not have any effect on the surface charge of the composite.

In an aspect, the mixed solution of the polymers is then added into a solvent (e.g. polyvinyl alcohol) and stirred for the particles to harden. In an aspect, the mixture is stirred for a few minutes to a few hours, or in a preferred aspect from about 2 hours to about 5 hours. Beneficially, the stirring permits the volatile solvent to evaporate and result in the hardened composites. The composites can then be separated, such as by filtration or centrifugation. The can then be further washed, and then dried or lyophilized until further use.

In a further embodiment of synthesizing the incorporation of the antigen or vectors is provided. A suspension of the antigen or vectors can be added directly to the first polymer described herein, namely a suspension of the first particle described herein. In an aspect, the solution is sonicated to create the oil-in-water emulsion. Thereafter, the second polymer can be added to the emulsion. In an aspect, the solution is again sonicated to create the oil-in-water emulsion. The emulsion can then be added into a solvent (e.g. poly vinyl alcohol) and stirred for the particles to harden. In an aspect, the mixture is stirred for a few minutes to a few hours, or in a preferred aspect from about 2 hours to about 5 hours. Beneficially, the stirring permits the volatile solvent to evaporate and result in the hardened polymers of the. The can then be separated, such as by filtration or centrifugation. The composites can then be further washed, and then dried or lyophilized until further use.

As an exemplary embodiment of the polymers, a first polymer is PLGA. The degradation of PLGA occurs through bulk erosion due to hydrolysis. In other words, the PLGA particle swells with water and erosion occurs throughout its volume. Minimizing the swelling of the polymer (i.e. limiting water infiltration), would result in a reduction of the hydrolysis rate. While PLGA has been coated with polymers to control drug release kinetics, the resulting release duration has been limited to only hours. In these instances, the coating provides an additional barrier to drug release but does not significantly affect the bulk erosion of the PLGA polymers. Accordingly, in a preferred exemplary embodiment according to the invention, a second polymer is provided, such as chitosan, wherein such polymer has greater stability against hydrolysis. In such an embodiment, the positively-charged second polymer (e.g. chitosan) binds the first polymer PLGA and acts as a reinforcing agent to slow down the permeation of water and swelling that would otherwise release the antigen or viral vector of the composition. The polymers can be combined, such as by homogenous mixing to improve the mechanical stability of the formulation and retard degradation of the PLGA polymer.

A further exemplified embodiment comprises a first polymer (e.g. PLGA) and second polymer (e.g. chitosan), and a vaccine, including for example an antigen or vector, mixed together homogenously in a particle, such as shown in FIG. 3A. In such an embodiment, bulk erosion of the first polymer PLGA would lead to a slow, constant release of the vaccine and the concentration of the second polymer chitosan in the particle, as well as other properties of the PLGA, controls the rate of erosion.

A further preferred embodiment comprises a vaccine, including for example an antigen or vector, encapsulated in a core of the particles formed by a shell composed of a first polymer (e.g. PLGA) and a second polymer (e.g. chitosan) homogenously mixed, such as shown in FIG. 3B. In such an embodiment, initial degradation of the PLGA would not result in vaccine release until a sufficient porosity is developed to release the entire contents within the core—leading to a burst release of vaccine after a period of time. In an exemplary aspect, a burst release is achieved after a predetermined period of time, including at least 4 weeks, at least 5 weeks, at least 6 weeks, at least 7 weeks, at least 8 weeks, at least 3 months, at least 4 months, or at least 6 months, including all ranges therebetween.

A further preferred embodiment of the polymers, include an enzyme or catalytic agent (also referred to as a catalyst) that selectively degrades the second polymer of the composition or formulation. Such an enzyme or catalytic agent provides an internal control of the rate of erosion. A catalytic agent (or catalyst) can include an enzyme or other chemical that promotes polymer degradation.

In an embodiment, the enzyme or catalytic agent is contained within the core and/or within the polymer shell comprising the first polymer and the second polymer homogeneously mixed and coating the vaccine, such as shown in FIG. 3C. As the enzyme or catalytic agent works to degrade the second polymer (e.g. the stabilizing polymer such as chitosan), it modulates the rate of erosion of the first polymer (e.g. PLGA). In another aspect, the enzyme or catalytic agent can also act to degrade the first polymer. As one skilled in the art will ascertain, a higher concentration of the catalyst provides more rapid release of the vaccine from the particles. Exemplary combinations of the second polymer and potential enzyme and/or catalysts include, but are not limited to: Chitosan polymer and lysozyme, chitinase, chitosanase, β-N-acetylhexosaminidase, chitin deacetylase, and/or papain; alginate polymer and alginate lyases, and/or oligoalginate lyase; collagen polymer and collagenases, matrix metalloproteinases, and/or phenylalanine protease; Dextran polymer and Endo-dextranase; Polyester polymers and acid phosphatase, alkaline phosphatase, and/or cholesterol esterase; Carboxymethyl cellulose polymer and β-1,4-glucan glucanohydrolase, β-glucosidase, and/or β-1,4-glucan cellobiohydrolase; DNA and Deoxyribonuclease; RNA and Ribonucleases; and Proteins and Proteases, trypsin, and/or chymotrypsin. In a still further aspect, the enzyme can be an acid generating enzyme, a base generating enzyme, and/or the enzyme generates a free radical (e.g. reactive oxygen species).

A further preferred embodiment of the polymers for the composites comprises multiple concentric "shells" of the first and second polymers encapsulating a vaccine, as shown in FIG. 3D. In such an embodiment, the vaccine may be distributed into the various shells to provide serial release of vaccine or it may be located within the core of the shells used to control the release kinetics. The polymers mixed with PLGA (or an alternative first polymer) may be the same polymers in the various layers at different concentrations (to vary the degradation rate) or may be different polymers altogether. Additionally, an enzyme or catalytic agent may be included in the layers to control degradation rates.

In a further exemplary aspect of the invention, a first polymer is hydrophobic and the second polymer is an enzyme substrate, such as for example chitosan. In such an embodiment, the particle can further include an enzyme or catalytic agent. In an embodiment, the catalytic agent can be active at physiological temperatures but inactive at temperatures above or below physiological temperatures. In a further embodiment, the catalytic agent is inactive until introduced to an activating co-factor or enzyme. Such an activating co-factor or enzyme can either be present in an animal body (i.e. the subject administered the composition or formulation) or the particle comprises the co-factor or enzyme. In an exemplary embodiment, lysozyme can be used to degrade peptidoglycans, which could be utilized as an enzyme found within the body of the subject being administered the compositions according to the invention. In a further exemplary embodiment, chitinase can be used to hydrolyze chitosan as disclosed by Zhang et al. in Biomaterials. 2001 June; 22(12): 1653-8. In vitro degradation of chitosan by a commercial enzyme preparation: effect of molecular weight and degree of deacetylation.

The preferred first polymer of PLGA can be further modified to control release kinetics of the active agent, such as a vaccine, through modulating the ratio of lactic to glycolic acid in PLGA polymer, varying the molecular weight of the second polymer (e.g. stabilizing polymer), varying the chemistry of the polymers (e.g. deacetylation degree of chitosan), and/or the inclusion of other additional stabilizers with the polymers (e.g. trehalose, mannitol, sucrose, PEG, etc.). In an aspect, modulating the ratio of lactic to glycolic acid in the PLGA polymer can extend the delayed release from days to months to at least 6 months.

In an embodiment, the particles comprise from about 50 wt-% to about 99 wt-%, from about 75 wt-% to about 99 wt-%, or from about 75 wt-% to about 90 wt-% of the first polymer, namely the hydrophobic polymer. In an embodiment, the particles comprise from about 50 wt-% to about 99 wt-%, from about 75 wt-% to about 99 wt-%, or from about 75 wt-% to about 90 wt-% of the PLGA polymer.

In an embodiment, the particles comprise from about 1 wt-% to about 50 wt-%, from about 1 wt-% to about 40 wt-%, or from about 1 wt-% to about 25 wt-% of the second polymer, namely the hydrophilic polymer. In an embodiment, the particles comprise from about 1 wt-% to about 50 wt-%, from about 1 wt-% to about 40 wt-%, or from about 1 wt-% to about 25 wt-% of the chitosan polymer.

In embodiments, the first and second polymer are present in a ratio of about 1:1, or in a range from about 0.1:1 to about 1:0.1, from about 0.2:1 to about 1:0.2, from about 0.3:1 to about 1:0.3, from about 0.4:1 to about 1:0.4, from about 0.5:1 to about 1:0.5, from about 0.6:1 to about 1:0.6, from about 0.7:1 to about 1:0.7, from about 0.8:1 to about 1:0.8, from about 0.9:1 to about 1:0.9, including all ranges of ratios therebetween.

In embodiments, the present biodegradable polymeric composite particles are from about 10 nanometers (nm) to about 100 micrometers (micron or μm), about 10 nm to about 75 μm, about 10 nm to about 50 μm, about 10 nm to about 25 µm, about 10 nm to about 10 µm, about 10 nm to about 5 µm, about 10 nm to about 1000 nm, about 20 nm to about 1000 nm, about 50 nm to about 1000 nm, about 100 nm to about 1000 nm, about 100 nm to about 750 nm, about 100 nm to about 500 nm, about 500 nm to about 1000 nm, about 500 nm to about 100 µm, about 500 nm to about 10 µm, about 1 µm to about 100 µm, about 1 µm to about 50 m, about 5 µm to about 50 µm, about 5 µm to about 25 µm, or about 5 µm to about 10 µm, including all ranges therebetween.

Active Agent

In embodiments, the present biodegradable polymeric composite particles comprise an active agent. In embodiments, the active agent is selected from a vaccine (including both vaccines to infectious diseases and non-infectious diseases such as cancer), a therapeutic, an immune mediator, a probiotic, a pharmaceutical, a vitamin, an adjuvant, or a cancer antigen.

In some embodiments, the active agent is a therapeutic agent. In some embodiments, the active agent is an immune mediator such as anti-CTLA-4 antibodies or anti-PD-1 antibodies. In some embodiments, the active agent is a probiotic such as *Lactobacillus* or *Bifidobacterium*. In some embodiments, the active agent is a pharmaceutics such as insulin, chemotherapeutics such as doxorubicin, morphine, or hormonal contraception. In some embodiments, the active agent is a vitamin such as vitamin A, vitamin D, or vitamin B12. In some embodiments, the active agent is an adjuvant such as aluminum salts squalene. In some embodiments, the active agent is a cancer antigen such as glycoprotein 70 or Cancer antigen 125 (CA-125). In some embodiments, the active agent is a cancer vaccine such as human papillomavirus (HPV) or hepatitis B virus (HBV). In some embodiments, the active agent is an antigen or viral vector composite. As referred to herein, a "vaccine" can include an antigen or vector, along with other components of a vaccine formulation, including for example adjuvants, slow release compounds, solvents, etc. Although vaccines are traditionally used to prevent or treat infectious diseases, vaccines are also able to modify the function of metabolites by binding signaling peptides or proteins or their receptors and by blocking antigens unique to certain abnormal cell types, such as for example, tumors. Accordingly, it is an embodiment of the invention provide vaccines to improve immune response to any antigen regardless of the antigen source or its function, including antigens to alter physiological functions that are desirable to improve health, such as immunizing against a hormone or protein for reproductive fertility.

As referred to herein, a "vector" carries a genetic code for an antigen, however it is not the antigen itself. In an exemplary aspect, a vector can include a viral vector or bacterial vector, such as spores. As referred to herein an "antigen" means a substance that induces a specific immune response in a subject, including humans and/or animals. The antigen may comprise a whole organism, killed, attenuated or live; a subunit or portion of an organism; a recombinant vector containing an insert with immunogenic properties; a piece or fragment of DNA capable of inducing an immune response upon presentation to a host animal; a polypeptide, an epitope, a hapten, or any combination thereof. Alternately, the immunogen or antigen may comprise a toxin or antitoxin. In various aspects, the antigen is a virus, bacterium, or a subunit of an organism.

In an aspect, the antigen induces an immune response against pathogens, including for example a virus. Exemplary viruses include an orthomyxovirus, a paramyxovirus, a rhinovirus, coronavirus, influenza virus, respiratory syncytial virus (RSV), a common cold virus or measles virus, herpes virus, rabies virus, varicella or other known viral pathogens.

In an exemplary aspect, the viral vector is an adenovirus, including for example wherein the adenovirus is a bovine adenovirus, a canine adenovirus, a non-human primate adenovirus, a chicken adenovirus, or a porcine or swine adenovirus. In a further aspect, the adenovirus can include a human adenovirus.

In a further aspect, the antigen induces an immune response against bacterial pathogens. Exemplary bacteria include *Bacillus, Mycobacterium, Staphylococcus, Streptococcus, Pseudomonas, Klebsiella, Haemophilus, Mycoplasm* and/or *Bacillus anthracis*. In a further aspect, the antigen an induce an immune response against a fungal pathogen. Exemplary fungus include *Aspergillus, Candida, Cryptococcus, Histoplasma, Pneumocystis*, and/or *Stachybotrys*.

In a further aspect, the antigen can include an allergen or a tumor associated antigen. In a still further aspect, the antigen may include polypeptides, peptides, or panels thereof that comprise one or more epitopes of a protein associated with a disease. For example, suitable polypeptides, peptides, or panels thereof may comprise one or more epitopes of a protein associated with a pathogen. Suitable polypeptides may comprise the full-length amino acid sequence of a corresponding protein of a pathogen or a fragment thereof. Further suitable antigens for the compositions, formulations and/or kits, and methods may include panels of peptides derived from a protein of a pathogen.

In a preferred aspect, the compositions and formulations include a vector, namely a viral vector. As referred to herein a viral vector is an engineered virus that incorporated genes for and express an antigens Vectors may be non-replicating and are safe for the host and environment. It should be appreciated that any viral vector may be incorporated into the compositions, formulations and methods of the invention to effectuate delivery into a cell. Use of viral vectors as delivery vectors are known in the art, including for example U.S. Pub. 2009/0017543 to Wilkes et al., the contents of which are incorporated by reference.

Exemplary viral vectors include adenovirus, retrovirus, lentivirus, herpes virus, pox virus, alpha virus, adeno-associated viruses, among others. Many such viral vectors are available in the art. The vectors described herein may be constructed using standard recombinant techniques widely available to one skilled in the art. Such techniques may be found in common molecular biology references such as Molecular Cloning: A Laboratory Manual (Sambrook, et al., 1989, Cold Spring Harbor Laboratory Press), Gene Expression Technology (Methods in Enzymology, Vol. 185, edited by D. Goeddel, 1991. Academic Press, San Diego, Calif.), and PCR Protocols: A Guide to Methods and Applications (Innis, et al. 1990. Academic Press, San Diego, Calif.). In an aspect, adenoviral vectors are particularly useful for gene transfer into eukaryotic cells and vaccine development, and in animal models.

Compositions and Formulations

In embodiments, the present pharmaceutical compositions comprising a present biodegradable polymeric composite particle provides a delayed release, such as a boost dose, of a vaccine. In certain other embodiments, the present pharmaceutical compositions comprising both a biodegradable polymeric composite particle and an active agent (e.g. vaccine, including both vaccines to infectious diseases and non-infectious diseases such as cancer) that is not encapsulated or stabilized with a polymer provides both an initial dose, such as a prime vaccine dose, and a delayed release, such as a vaccine boost dose. The delayed dose may be delivered as a burst or bolus dose during a period of about 7 days to 6 months after administration. In embodiments, the delayed dose is delivered about 7 days to 5 months, about 7 days to 4 months, about 7 days to 3 months, about 7 days to 10 weeks, about 7 days to 8 weeks, about 7 days to 6 weeks, about 7 days to 4 weeks, about 7 days to 3 weeks, or about 7 days to 14 days after administration. In certain embodiments, the delayed dose is delivered about 14 days to 4 months, about 14 days to 12 weeks, about 14 days to 10 weeks, about 14 days to 8 weeks, about 14 days to 6 weeks, about 14 days to 4 weeks, or about 14 days to 21 days after administration.

In embodiments, provided herein are pharmaceutical compositions comprising a) a present biodegradable polymeric composite particle; and, b) a vaccine or therapeutic composition that is not encapsulated or otherwise stabilized by a polymer. In other embodiments, provided herein are pharmaceutical compositions comprising a) a present biodegradable polymeric composite particle wherein the particle encapsulates an active agent.

In an aspect of the invention, the compositions and formulations include an antigen or a vector that contains and expresses an antigen encapsulated in or incorporated into a biodegradable polymeric composites comprising at least a first polymer with a first rate of degradation and a second polymer with a second rate of degradation, and wherein the composite is configured to induce a prolonged time to boost delivery of the antigen or vector. In an aspect, the particle comprises at least a first polymer with a first rate of degradation that serves to form a solid matrix to encapsulate the antigen or vector and a second polymer with a second rate of degradation that is different from the first rate of degradation, to serve as a binder that modulates overall degradation rate of the particle and induce a prolonged time to boost delivery of the antigen or vector. The compositions can further provide an antigen or a vector that is not encapsulated in or incorporated into the biodegradable polymeric particle in order to provide an initial or prime delivery of the antigen or vector.

The compositions and formulations can include the various particles and/or composites described herein. In an aspect, the polymers can be formulated in a homogenous mixture thereof. Beneficially, the combined use of the antigen or a vector with the polymeric composite provides superior immune response in comparison to the antigen or vector alone. The composition and formulations include an effective amount or concentration of the antigen and/or vector for inducing a protective or therapeutic immune response against a pathogen or disease.

In some embodiments, the compositions and formulations include an enzyme and/or catalytic agent. In an embodiment, the enzyme or catalytic agent selectively degrades one or more of the polymer of the composition or formulation. Such an enzyme or catalytic agent provides an internal control of the rate of erosion. A catalytic agent (or catalyst) can include an enzyme or other chemical that promotes polymer degradation.

In some embodiments, the compositions and formulations include an adjuvant. Adjuvants include, for example, compound(s) that enhances the immune response to an antigen and/or vector. Examples of adjuvants which may be employed include but are not limited to, co-polymer adjuvants, lipopolysaccharide adjuvants, oligonucleotide adjuvants (e.g. CpG), incomplete Freund's adjuvant, saponin, mineral gels such as aluminum hydroxide, surface active substances such as lysolecithin, pluronic polyols, polyanions, peptides, oil or hydrocarbon emulsions in water, and the like. Additional adjuvants can include, for example, monophosphoryl lipid A. Still further exemplary adjuvants may include preservatives and/or anti-microbial or anti-bacterial agents, such as benzalkonium chloride).

In some embodiments, an adjuvant that is coencapsulated with an antigen will promote and enhance the hosts immune response to the antigen. Examples of such adjuvants include oligoneucleotides such as CpG that induce innate immunity, anti-tumor activity and activation of Toll-like receptors. CpG-like Toll-Like Receptor (TLR) 9 has been found to be the primary receptor for CpG ODN. The complex immunologic responses to CpG ODN by various immune cells results in the activation of NK cells, T cells, B cells, monocytes, macrophages and dendritic cells.

In some embodiments, the compositions and/or pharmaceutical formulations include a pharmaceutically acceptable excipient, diluent, carrier and/or adjuvant.

In some embodiments, the pharmaceutical formulations can include a vaccine. In other embodiments, the pharmaceutical formulations can be provided as a kit for preparing a vaccine composition. For example, a kit may include a lyophilized antigen and/or viral vector prepared according to the compositions and methods described herein, and a pharmaceutical solution comprising a carrier, diluent, excipient, and/or adjuvant for combining with the lyophilized antigen and/or vector to prepare the vaccine. The kit may optionally include directions for preparation and/or use.

In some embodiments, the compositions and/or pharmaceutical formulations include bioprotectants, such as albumin, trehalose, mannitol, dextran, sucrose, or others having demonstrated stabilizing effects. Additional stabilizing agents can be included, such as carbohydrates and polyalcohols to prevent heat denaturation and enhance stability, and/or trehalose and dextran to inhibit virus aggregation, and/or mannitol to inhibit free-radical oxidation of the virus. An exemplary method of utilizing stabilizing agents in the methods of encapsulating a vaccine using the compositions disclosed herein would include addition of the stabilizing agents with the adenovirus during formation of the water-in-oil emulsion. In a non-limiting embodiment, the polymers are mixed, in particular mixed until they can no longer separate in a liquid phase. Thereafter a solvent can be evaporated to harden the PLGA (first polymer) and effectively trapping the chitosan (second polymer) in the composite material. The polymers can be homogenously distributed or concentrated in the polymer structure, such as the outer shell of the structure. The antigen or viral vector can be encapsulated within such polymer structures.

The compositions and/or pharmaceutical formulations can be provided in a liquid, suspension, emulsion and/or lyophilized form. In preferred aspects, lyophilized forms of the compositions and/or pharmaceutical formulations can be stored at ambient conditions and suspended in water before injection, eliminating the need to maintain cold storage to preserve potency.

Methods of Use

In embodiments, the pharmaceutical compositions are used for delivering an antigen or vector for treating or preventing an infection or a disease caused by a pathogen or a non-pathogen target. In embodiments, the present pharmaceutical compositions are used to deliver a delayed dose, to an animal in need thereof, either as a standalone delayed delivery dose or in combination with an active agent that is not encapsulated or stabilized with a polymer providing a bi-phasic delivery of an active agent. In embodiments, the bi-phasic delivery of active agent may be used to simulate a prime/boost dose delivery of a vaccine (including both or either a vaccine to an infectious disease or a non-infectious disease vaccine), wherein the initial prime dose in the pharmaceutical formulation is not encapsulated and delivered when the composition is delivered to the animal and the delayed or boost dose is encapsulated in the particle and delivered at a time period at least 7 days after the administration of the composition. Hence, provided herein are methods for delivering an initial prime dose and delayed boost dose in a single administration dose, comprising administering a pharmaceutical composition comprising a) the present biodegradable polymeric composite particles and b) a vaccine or therapeutic composition that is not encapsulated or stabilized with a polymer, to an animal in need thereof.

In alternative embodiments, the pharmaceutical composition is used to deliver only a delayed dose to an animal. In this instance, the delayed dose may comprise a vaccine or a therapeutic. In one embodiment is provided a method for delivering a vaccine to a neo-natal animal, comprising delivering the present biodegradable polymeric composite particles wherein the active agent is a vaccine composition and the particle comprises at least one coating comprising at least a second polymer configured for at least a first and second delayed release of the vaccine composition during a period of 7 days to 6 weeks. The coating comprising the vaccine and second polymer provided for a serial and subsequent release of vaccine at pre-determined intervals of time, such as weekly.

In an aspect of the invention, the compositions, formulations and methods of use thereof described herein beneficially provide for administration of a single dose therapeutic or prophylactic and eliminate the need for reimmunization as required for traditional vaccines. In an aspect of the invention, the compositions, formulations and methods of use thereof described herein provide a vaccine employing particles to release an antigen or vector at predetermined intervals after a single injection that mimics the effect of reimmunization and sustains the durability of protection. In a further beneficial aspect, the compositions, formulations and methods of use thereof described herein encapsulate a vaccine to achieve extended-release of vaccines that will produce protective antibody concentration (as can be measured by a titer). In a further beneficial aspect, the compositions, formulations and methods of use thereof described herein produce an enhanced immune response in a subject by protecting vaccines from host degradation and permitting targeting of specific immune mediating cells. In a still further beneficial aspect, the compositions, formulations and methods of use thereof described herein provide improved immune responses to weak antigens, thereby expanding the number and types of diseases suitable for treatment and prevention.

In some aspects of the invention, the methods for treating or preventing an infection or pathogen can include providing a prolonged protective immune response lasts for years. In additional aspects, the methods include delivery of particles configured to release one or multiple antigens or viral vectors at specific intervals which are capable of inducing a protective immune response. In an exemplary embodiment, encapsulated antigens or vectors are prevented from degradation following administration to a subject for a predetermined period of time, including for at least 4 weeks, at least 5 weeks, at least 6 weeks, at least 7 weeks, at least 8 weeks, at least 3 months, at least 4 months, or greater, including all ranges therebetween.

The various methods of use are suitable for administering the compositions to animals. The methods are particularly suitable for use in humans, including for example, to treat and prevent a variety of pathogens. The methods are further suitable for use in treating a variety of animals to treat and prevent a variety of pathogens. In an aspect, the compositions are suitable for treating mammals, birds, and like, including domesticated, wild, feral and commercial livestock. In a further aspect of the invention for use in animals, the compositions and methods of use thereof described herein beneficially limit the need to handle grazing range herds frequently, thereby avoiding vaccine failures caused by non-compliance with vaccines requiring repeated immunizations, and reducing dependence on cold storage to maintain biopotency of vaccine compositions.

The compositions and formulations described herein can be administered in various invasive or non-invasive routes. As an example, the compositions and formulations can be administered to a subject by parenteral routes, oral routes, mucosal routes, topical routes, intranasal routes or any other route of administration.

In an embodiment, the methods may be utilized for inducing a protective and/or therapeutic immune response against a pathogen and/or disease by administering the compositions described herein (e.g., as immunogenic compositions or vaccines) to a subject in need thereof. As referred to herein, inducing an immune response may include reducing the pathogenic load of a subject, for example, as determined by measuring the amount of circulating pathogen before and after administering the composition. Inducing an immune response may include reducing the degree or severity of at least one symptom of infection by the pathogen. Inducing an immune response may further include eliciting a cellular immune response, such as a Th1-response, which may be characterized by cytokine production such as interferons, tumor necrosis factors, interleukins, and/or presence of opsonizing antibodies against the antigen.

EXAMPLES

Embodiments of the present invention are further defined in the following non-limiting Examples. It should be understood that these Examples, while indicating certain embodiments of the invention, are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

The disclosure of each reference set forth herein this patent application is incorporated herein by reference in its entirety.

Animal Immunization Procedures:

Formulations that showed the desired release kinetics and stability in vitro were tested for immunogenicity in mice for safety and efficacy. Mouse screening is used to characterize the immune and durability characteristics of the controlled release formulation compared to non-encapsulated vaccines. Animals were necropsied with collection of serum for antibody assays. The injection site and visceral organs were examined for lesions and any suspected abnormalities were fixed in neutral buffered formalin and processed for microscopic examination and histopathological assessment.

Antibody Assays:

The in vivo antibody response to the vaccine, i.e., immunogenicity, were assessed using the standard assays appropriate for the vaccine antigen.

Bioavailability Assays:

Bioavailability of encapsulated vaccine that were tested in vitro. The concentration of adenovirus vector was determined using quantitative real-time PCR targeting the boundary of the transgene and the flanking sequences. Vaccine that is either encapsulated in particles or released into surrounding medium were extracted prior to quantification. Purified vaccine used during the encapsulation process serve as a calibrator and spiked into the sample prior to extraction to verify extraction efficiency and detect any matrix effects during quantification of the vaccine or antigen.

Stability Assays:

The biological activity of encapsulated and released vector were determined using a focus forming assay wherein the concentration of biologically active vector particles is assayed by enumerating the number of infected cells 48 hours after a series of sample dilutions are inoculated onto permissive cells. Infected cells are identified by the intracellular staining of the adenovirus hexon protein with antibody conjugated to a chromophore or fluorescent moiety, alternatively, other vaccines antigens are enumerated using assays relevant to the vaccine antigen. Vaccines encapsulated in particles that are released/extracted are assayed by methods appropriate to the specific vaccine or antigen. By combining the results of these two analyses, the concentration and activity of the vector encapsulated in particles and released into the medium was accurately determined and used to express the release rates and stability of the various formulations.

Example 1

Synthesis of PLGA and PLGA-Chitosan Composite Particles

Materials and Methods:

Green fluorescent protein (GFP)-expressing adenovirus suspended in DMEM culture media was purchased from Vector Biolabs, Inc., Malvern, Pa., USA; Poly-lactic glycolic acid (PLGA) (lactic acid to glycolic acid ratio (also referred to as lactic to glycolic ratio): 50:50) (molecular weight: 30-60 kD), Chitosan (molecular weight: 50-190 kD) (degree of deacetylation: 75-85%), Dichloromethane, Polyvinyl Alcohol (PVA), acetic acid was purchased from Sigma-Aldrich Co.

PLGA and PLGA-chitosan composites were prepared by modifying the solvent evaporation method. To produce PLGA particles, 20 mg of PLGA was dissolved in dichloromethane (DCM) to form 1 wt % solution of PLGA. PVA solution (5 ml of 1 wt %) was added to this and the resulting solution sonicated at a 5% amplitude to get an oil-in-water (O/W) emulsion. This initial emulsion was slowly added to 25 ml of 1 wt % PVA and the resulting emulsion stirred for 3 hours to evaporate the DCM and harden the particles.

PLGA-chitosan composite (referred to in the figures as "composites") particles were formed by adding 20 mg PLGA in DCM to 20 mg of chitosan dissolved in 0.1M acetic acid. This solution was sonicated and then 5 mL of 1 wt % PVA added. The resulting emulsion was added to 25 mL of PVA and stirred for 3 hours to evaporate the DCM. Recovered particles were washed with DI water several times and stored at −20° C. for further analysis.

Particles were characterized using Fourier transform infrared spectroscopy (FTIR-4200, Jasco International Co., Ltd., Tokyo, Japan). Two mg of each sample was mixed with 200 mg potassium bromide and the mixture compressed into a KBr disc. Each KBr disc was scanned over a wavenumber region of 650-4,000 $cm^{-1}$ with a resolution of 4 $cm^{-1}$. Hydrodynamic Diameter and surface charge of the particles were measured via dynamic light scattering analysis (Zeta Sizer Nano-ZS from Malvern Instruments, Malvern, UK). The particles were dispersed in DI water and measurements were carried out at 25° C. The morphology of PLGA, PLGA-Chitosan composites and adenovirus encapsulated in both PLGA and composites were examined by scanning electron microscopy (Zeiss EVO50) at an accelerating voltage of 20 kV. Particles were gold coated and mounted on aluminum stubs.

Figure 5:
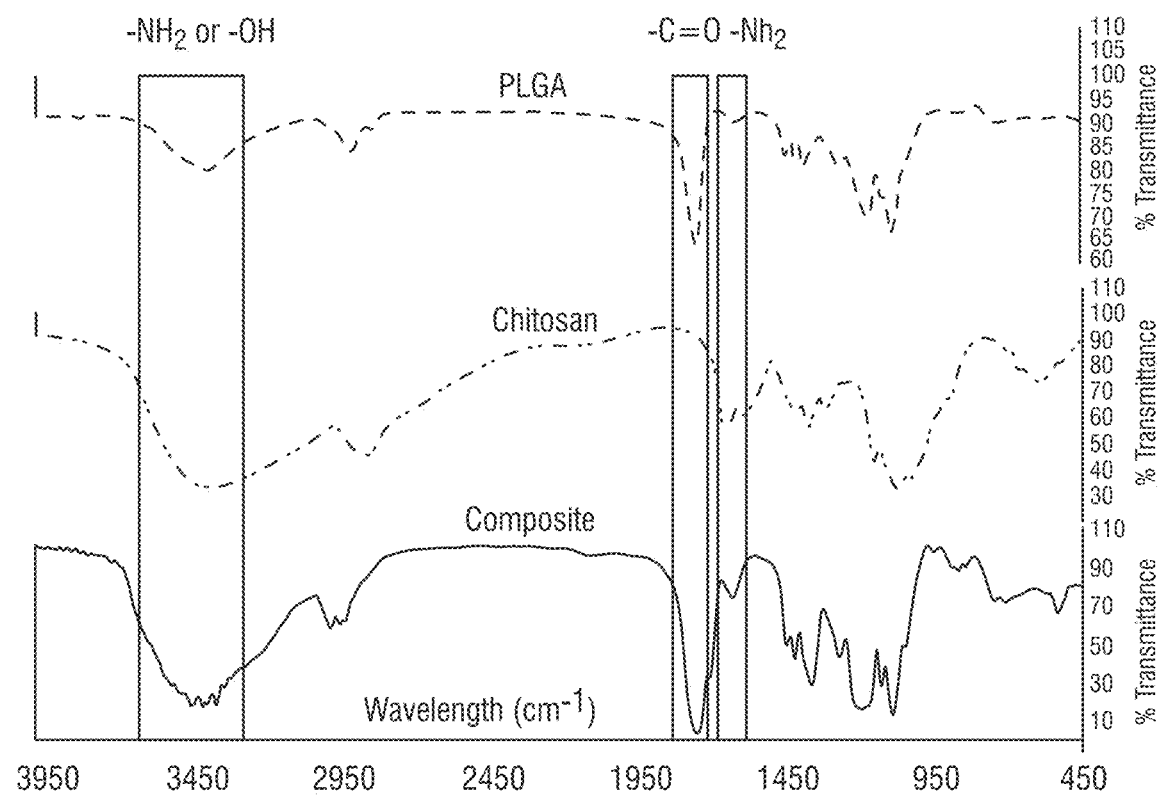
FIG. 5 illustrates the respective bond stretching with primary amine bond stretching representing the presence of chitosan and carboxylic acid (=O) stretching signifying the presence of PLGA demonstrating the composite may contain both polymers according to embodiments of the invention.

Results:

FIG. 5 shows infrared spectra for the pure polymers as well as the composite. The figure illustrates the respective bond stretching with primary amine bond stretching representing the presence of chitosan and carboxylic acid (=O) stretching. The peaks at 1755 $cm^{-1}$ were identified as stretching vibrations of —C=O in PLGA. The peaks at 3450 $cm^{-1}$ and 1620 $cm^{-1}$ are due to stretching vibrations from —NH in chitosan. The results show the presence of PLGA demonstrating the composite can contain both polymers according to embodiments of the invention.

Figure 6A:
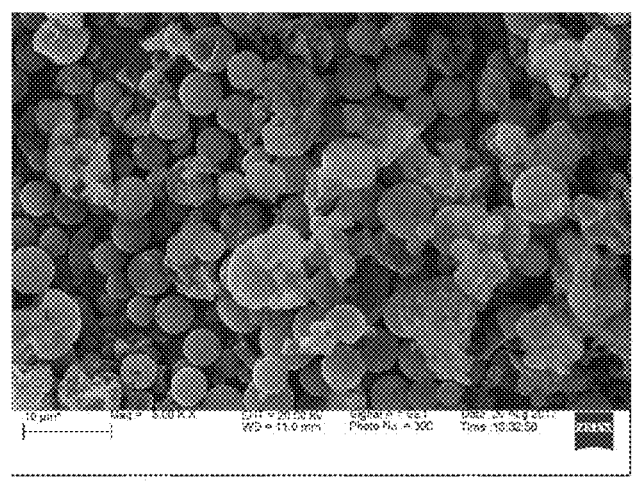
FIGS. 6A-6D show scanning electron micrographs of adenovirus vaccines encapsulated in particles according to embodiments of the invention, where
Figure 6B:
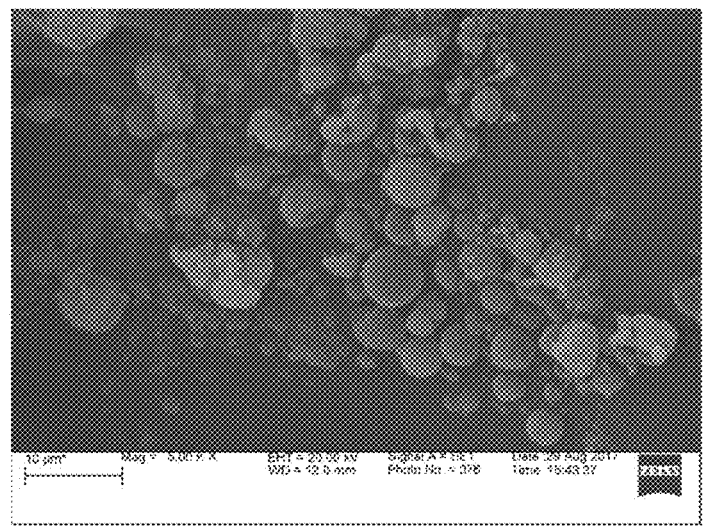
Figure 6C:
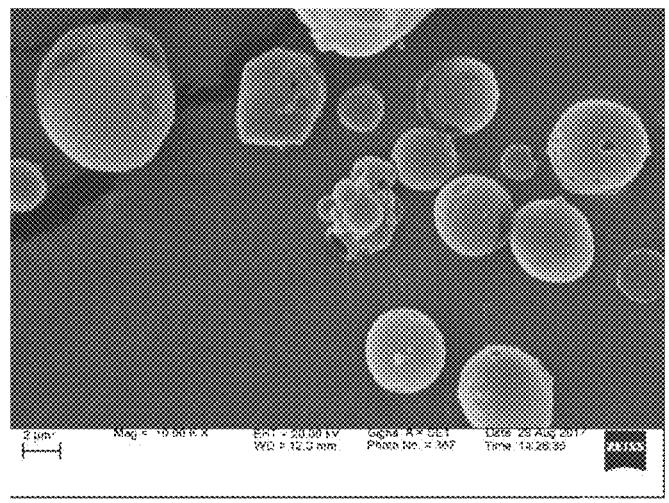
Figure 6D:
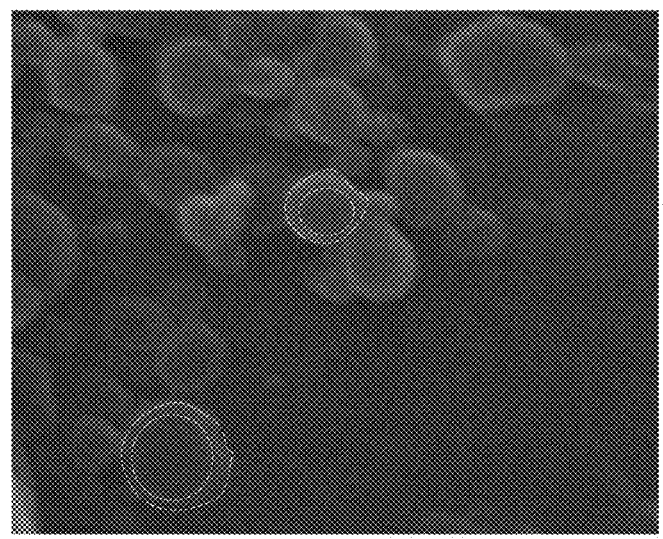

FIGS. 6A-6D shows the scanning electron micrographs of the various particles obtained from the synthesis procedure. FIGS. 6B and 6D show expanded views of FIGS. 6A and 6C, respectively. These photomicrographs show the various morphologies (spherical, porous, hollow) that can be obtained and determine the release profiles of vaccines. The results confirm the ability to control the surface morphologies of the particles formed by changing the solvent evaporation rate. Without being limited to a particular mechanism of action, the surface morphologies impact the release profiles of the delivery systems.

Example 2

Encapsulation of Adenovirus in a PLGA-Chitosan Composite

Adenovirus Vectored Vaccine Selection, Construction and Production:

For purposes of illustrating the ability to employ composites for controlled delivery of vaccines, the well characterized anti-influenza adenovirus vectored vaccine was employed as the prototype as it is readily available and treatment for influenza, an important pathogen of both animals and humans. The prototype vector AdPNM.H3 was utilized in the examples. This vector utilizes an E1/E3-deleted adenovirus type 5 vaccine vector background and expresses the hemagglutinin (HA) protein from the Panama/2007/99 strain of H3N2 human influenza virus. This vector has been studied and characterized extensively and is known to be immunogenic in mice. The vector is easily produced in 293HEK cells and the in vivo activity of the vector can be determined in mice by measuring the immunogenicity of the vaccine by standardized methods including hemagglutinin inhibition (HAI or HI) and microneutralization.

A 200 μl solution of green-fluorescent protein (GFP) expressing adenovirus ($1 \times 10^{10}$ PFU/ml) was added to 2 mL of 1 wt % PLGA solution in dichloromethane (DCM) and the solution sonicated for 15 seconds to create a water-in-oil (W/O) emulsion. To this emulsion was added 2 mL of 1 wt % chitosan dissolved in acetic acid and sonication conducted for 30 seconds. The solution was then added dropwise to 25 mL of 1 wt % of PVA solution and stirred for 3 hours under negative air pressure to remove the volatile DCM. Particles were washed four times, by centrifuging at 10,000 rpm and resuspending in ultrapure water, and then lyophilized.

Results:

The particles were analyzed by dynamic light scattering (DLS) to determine their hydrodynamic diameters. Furthermore, the surface charge of the particles was measured by zeta potential measurements. Results for adenovirus-loaded particles and composite particles without the virus are provided in Table 1.

TABLE 1

|  | Adenovirus-loaded Composite | Composite |
|---|---|---|
| Vol of virus:Vol of PLGA (mL/mL) | 0.17 | 0 |
| Average Diameter (nm) | 1666 | 1614 |
| Average zeta potential (mV) | −4.36 | 33.57 |

Although the adenovirus-loaded composite and the non-loaded composite particles had similar average sizes, there was a dramatic difference in the surface charge. The composite particles should a positive surface charge, which was expected due to the cationic nature of chitosan. Particles loaded with the adenovirus, on the other hand, showed a slight negative charge which is likely due to interactions with the adenovirus.

Figure 7:
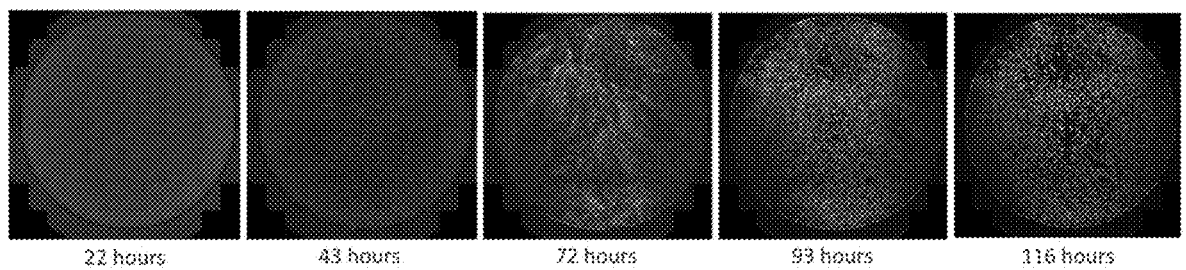
FIG. 7 illustrates preservation of viable vector over time with adenovirus vaccine vector encapsulated in PLGA and composites.

The viability of the encapsulated adenovirus was determined by incubating loaded particles with HEK 293 cells cultured in 24 well plates. The appearance of fluorescent foci, shown in FIG. 7, confirmed that infectivity of the adenovirus was retained during the particle synthesis. FIG. 7 illustrates adenovirus vaccine vector encapsulated in PLGA and composites with preservation of viable vector over time, with the vaccine encapsulated composite particles incubated with 293 Human Embryonic Kidney (HEK) cells and fluorescent focus assay was performed to demonstrate viable vaccine vectors.

Example 3

Demonstration of Bioactivity of Encapsulated Adenovirus

Human embryonic kidney cells (293 HEK) were incubated with adenovirus encapsulated PLGA-chitosan particles at various particle concentrations ranging from 0.1 to 4 mg/mL in 24-well plates. At periods of 20, 43, 65, and 93 hours, the plates were imaged by fluorescence microscopy and the number of fluorescent foci in each well determined by analysis with ImageJ software.

Figure 8:
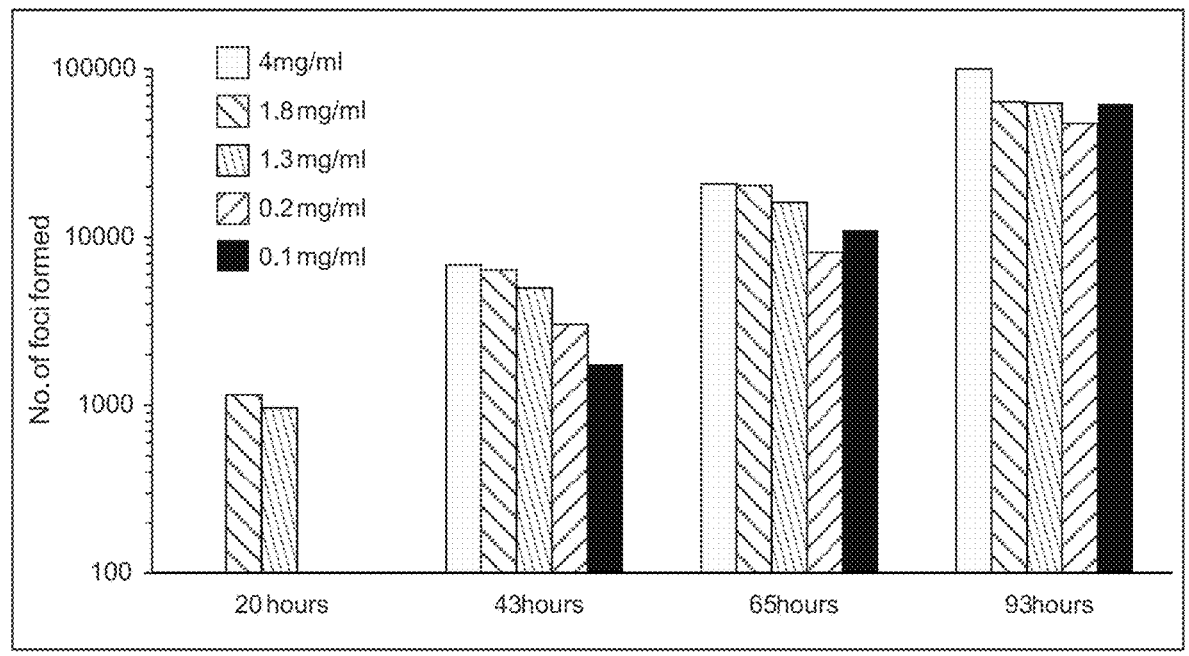
FIG. 8 depicts the concentration dependent cellular response to encapsulated GFP-expressing adenovirus according to an exemplary embodiment of the invention.

Results:

Fluorescent foci are developed when bioactive adenovirus is released from the particles, enters the cells and then initiates production of GFP. Data presented in FIG. 8 depicts the concentration dependent cellular response to encapsulated GFP-expressing adenovirus and shows a strong correlation between concentration of adenovirus-loaded particles added to the cell culture and the number of observed fluorescent foci formed. This demonstrates retention of some infectivity potential of the adenovirus and also suggests that the magnitude of response to the vaccine can be modulated.

The results illustrate that adenovirus vector incorporated with particles retains bioavailability of the antigen in the host. Beneficially, the compositions and formulations employed retained the adenovirus vectors activity and this could be further enhanced by inclusion of stabilizing agents, such as trehalose or other preservatives.

Example 4

In Vivo Immunization Trial for Ad-Influenza-Nanoencapsulation.

Animal Immunization Procedures:

Formulations that show promise in vitro will be tested for immunogenicity in mice for safety and efficacy. Mouse screening will characterize the immune and durability characteristics of the controlled release formulation compared to non-encapsulated vaccines. The study consists of Phase I to confirm an optimal dose needed to distinguish the added benefit of encapsulated vaccine versus unencapsulated vaccine. Phase II is designed to determine the immune response and duration of an immune response of the encapsulated vaccine compared with the unencapsulated vaccine. Three different encapsulation formulations will be tested in Phase II.

Phase I Pilot Project to Determine Optimal Dose of Unencapsulated Ad-H2N2.

The goal was to select a dose that is minimally immunogenic after a single dose of the unencapsulated vaccine to maximize the contrast with the same dose administered with the encapsulated sustained release vaccine. Experimental groups include: Male outbred mice (Charles River CD1) approximately 30 days of age were assigned to control (3 mice/time point) or vaccinated (5 mice/time point). Unimmunized control mice: Mice dosed with buffer were injected subcutaneously once on day 0 with 100 ul of Buffer solution. Three mice were assigned per cohort, one cohort for each test dose and time, designated Buffer A,B,C. Immunized mice: Five mice per dose and time point cohorts were dosed with unencapsulated vaccine given as single dose administered subcutaneously on day 0 (100 ul volume). Dose are 10×5, 6, 7, 8 Infectious particles administered subcutaneous (SQ). Each dose cohort was killed for Ab testing at 30, 60 and 90 days after single dose. The injection site and visceral organs were examined for lesions and any suspected abnormalities will be fixed in neutral buffered formalin and processed for microscopic examination and histopathological assessment.

The Results are shown in Table 2.

TABLE 2

| Dose 1 ml volume | Mouse | Antibody Titer 30 da. | Antibody Titer 60 da. |
|---|---|---|---|
| Buffer s.c. | Buffer A | <10 | <10 |
| Buffer s.c. | | <10 | <10 |
| Buffer s.c. | | <10 | <10 |
| 1E+06 ifu/mouse s.c. | Buffer B | 640 | 1280 |
| 1E+06 ifu/mouse s.c. | Buffer C | 160 | 320 |
| 1E+06 ifu/mouse s.c. | 10 × 6 C | 320 | 640 |
| 1E+06 ifu/mouse s.c. | 10 × 6 D | 480 | 160 |
| 1E+06 ifu/mouse s.c. | 10 × 6 E | <10 | 320 |
| 1E+107 ifu/mouse s.c. | 10 × 7 A | 240 | >1280 |
| 1E+07 ifu/mouse s.c. | 10 × 7 B | 1280 | 960 |
| 1E+07 ifu/mouse s.c. | 10 × 7 C | 1280 | >1280 |
| 1E+07 ifu/mouse s.c. | 10 × 7 D | 1280 | 480 |
| 1E+07 ifu/mouse s.c. | 10 × 7 E | >1280 | 640 |

TABLE 2-continued

| Dose 1 ml volume | Mouse | Antibody Titer 30 da. | Antibody Titer 60 da. |
|---|---|---|---|
| 1E+08 ifu/mouse s.c. | 10 × 8 A | 1280 | >1280 |
| 1E+08 ifu/mouse s.c. | 10 × 8 B | >1280 | >1280 |
| 1E+08 ifu/mouse s.c. | 10 × 8 C | 640 | >1280 |
| 1E+08 ifu/mouse s.c. | 10 × 8 D | 960 | >1280 |
| 1E+08 ifu/mouse s.c. | 10 × 8 E | 1280 | >1280 |

Results:

These results determined that the Optimal Dose to be used in the Comparison of Unencapsulated and Encapsulated Vaccines in Phase II should be $1\times10^6$ IFU/mouse S.C. No abnormalities were observed in any visceral organs.

Example 5

Vaccine Synthesis.

Materials and Methods:

Poly-lactic glycolic acid (PLGA) (50:50 ratio of lactic:glycolic), Chitosan (low molecular weight; 50-190 kD) were purchased from Sigma Aldrich, Dichloromethane, Acetic acid (0.1M), Poly vinyl alcohol (PVA) were all standard grade. Green Fluorescent Protein (GFP) expressing adenovirus (Ad-eGFP) was acquired from Vector BioLabs Inc.

Synthesis of PLGA Particles:

In a typical synthesis, 150 mg of poly-lactic glycolic acid (PLGA) (50:50) was dissolved in 1.5 ml dichloromethane (DCM) to make 10% (w/v) solution. 30 ml of 3% (w/v) of poly vinyl alcohol (PVA) was added to maintain a water-to-oil ratio of 20:1. This mixture was sonicated at 5% amplitude for 1 min to create an oil-in-water emulsion. This mixture was stirred for 4 hours to allow for DCM evaporation and hardening of the particles. After the stirring was completed, the particles were centrifuged at 10,000 rpm for 15 min and given 4 washes with DI water. 50 µl of 2% (w/v) trehalose in water was added as a lyoprotectant and the particles were further freeze dried for a day before using for further experiments.

Synthesis of PLGA-Chitosan Composite Particles:

PLGA, dissolved in DCM (10% w/v), and Chitosan, dissolved in 0.1 M acetic acid to a concentration of 1-3% w/v, were mixed together at a 1:1 ratio by volume. This solution was then added drop wise in 28 ml 3% PVA and the solution was stirred for 4 hours to harden the particles. After the stirring was completed, the particles were centrifuged at 10,000 rpm for 15 min and given 4 washes with DI water. 50 µl of 2% (w/v) trehalose in water was added as a lyoprotectant and the particles were further freeze dried for a day before using for further experiments.

Adenovirus Encapsulation in PLGA-Chitosan Composite Particles:

400 µl of adenovirus suspended in DMEM culture media was added to 1.5 ml of PLGA dissolved in DCM (10% w/v); this solution was sonicated at 5% amplitude for 15 secs to create an oil in water emulsion. 1.5 ml of chitosan (1% and 3% (w/v)) dissolved in acetic acid was added to this emulsion. The emulsion was sonicated again at 5% amplitude for 30 sec. This solution was then added drop wise in 28 ml of 1% PVA and the solution was stirred for 4 hours to let the DCM to evaporate. Particles formed were washed 4 times with water at 10000 rpm for 15 min. 50 µl of 2% (w/v) trehalose in water was added as a lyoprotectant and the particles were further freeze dried for a day before using for further experiments.

Figure 9A:
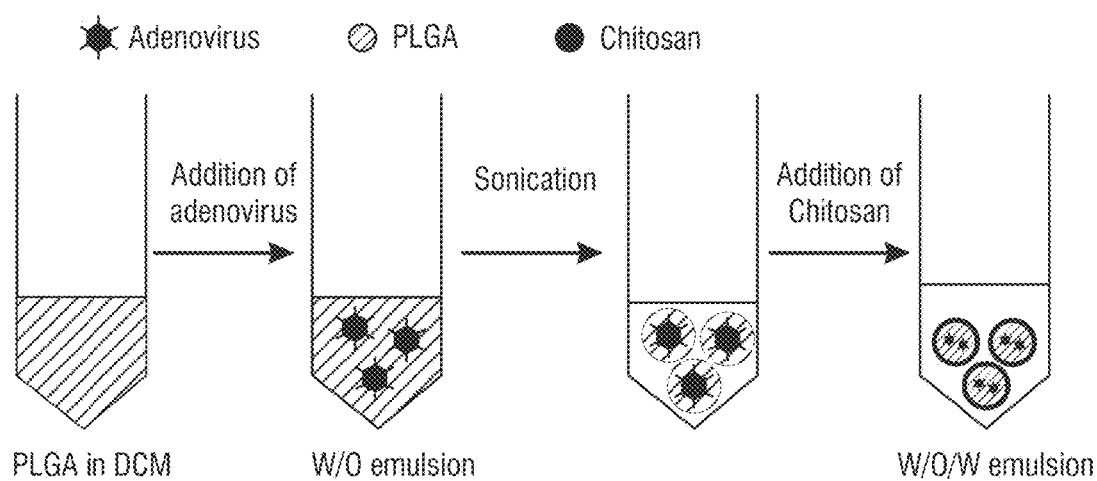
Figure 9B:
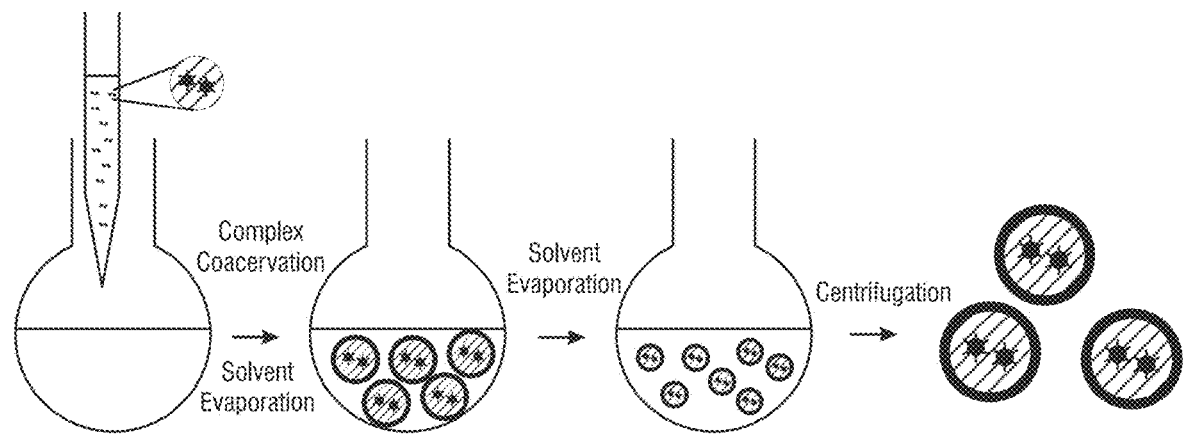

FIG. 9 shows an exemplary synthesis of the composite materials employed in embodiments of the invention as described herein this Example. FIG. 9A shows the formation of water in oil in water emulsion, and FIG. 9B shows the formation of the composite particles as they are hardened.

Characterization of Composite Particles:

Scanning Electron Microscopy:

A Zeiss EVO 50 SEM operating at a voltage of 20K are used to determine size distribution and surface morphology of the composite particles. Freeze dried composite particles were laden on a double-sided carbon tape which is mounted on Al-stub. These particles are further gold-coated and then imaged. The observation of surface morphology provides information on the formation and distribution of pores in the composite particles as they degrade to determine or select the release profile.

Dynamic Light Scattering (DLS):

The hydrodynamic diameter of composite particles was analyzed by DLS method using Malvern Zetasizer Nano ZS (Malvern, UK). The size of the composites was characterized by backscatter detection (173°). In addition, the surface charge of the particles (Zeta potential) was also detected by Malvern Zetasizer Nano ZS (Malvern, UK) using Smoluchowski model. (Journal of Controlled Release 235 (2016) 337-351; Schmitz, K. S. An introduction to dynamic light scattering by macromolecules. (Academic Press, 1990)).

Qualitative Determination of Chitosan in the Composite:

Fluorescein isothiocyanate (FITC) is a derivative of fluorescein used in wide-ranging applications. FITC is the original fluorescein molecule functionalized with an isothiocyanate reactive group (—N═C═S), replacing a hydrogen atom on the bottom ring of the structure. This derivative is reactive towards nucleophiles including amine and sulfhydryl groups. FITC has excitation and emission spectrum peak wavelengths of approximately 495 nm/519 nm, giving it a green color. Chitosan consists of a primary amine group and hence can be fluorescently tagged using FIT-C. Excess dye is removed by precipitating out chitosan by increasing the pH of the solution. This precipitated chitosan is separated by centrifugation and giving multiple washes using acetone. This fluorescently labelled chitosan is used to synthesize the composite particles for further characterization. The particles are further imaged under fluorescent microscope to confirm the distribution of chitosan in the composite.

Quantification of Total Encapsulated Virus:

1 mg of particles were dissolved in DCM overnight to extract the adenovirus encapsulated. To this solution of dissolved particles, 1 ml DNase free water was added and the DCM solvent was let to evaporate overnight at 400 C. The adenovirus released from the dissolved particles gets suspended in the aqueous phase and the adenoviral count is obtained using qPCR.

Figure 10A:
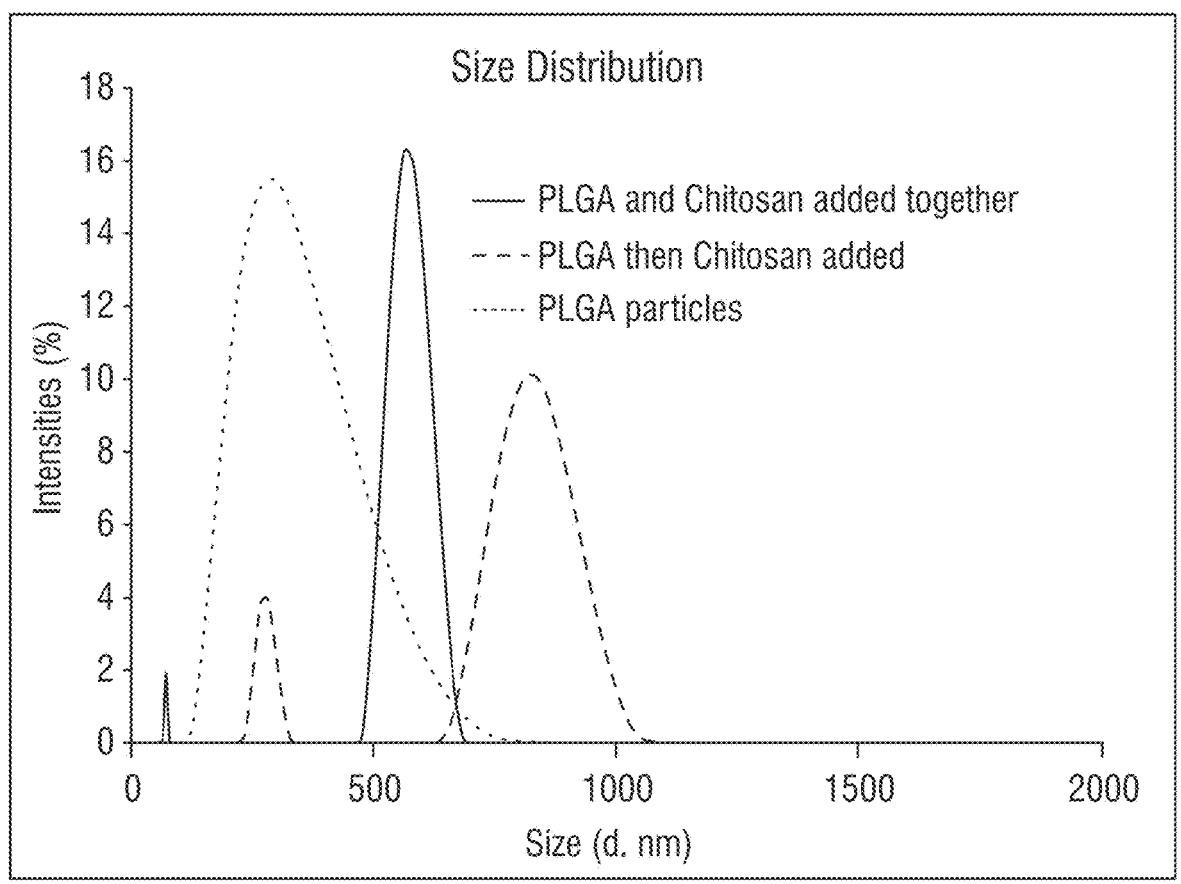
FIGS. 10A-10B show physical property distribution of example particles synthesized with different addition sequences, including pure PLGA particles having a negative surface charge and Chitosan having a positive surface charge.
Figure 10B:
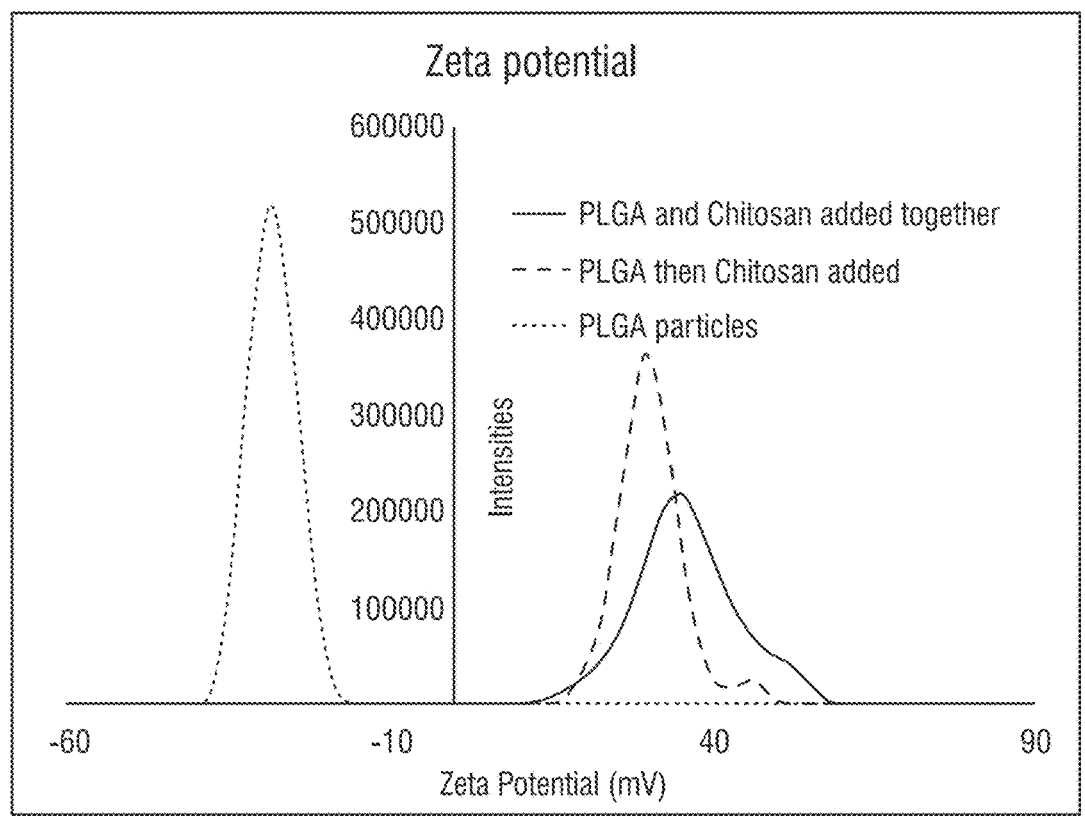
Figure 11A:
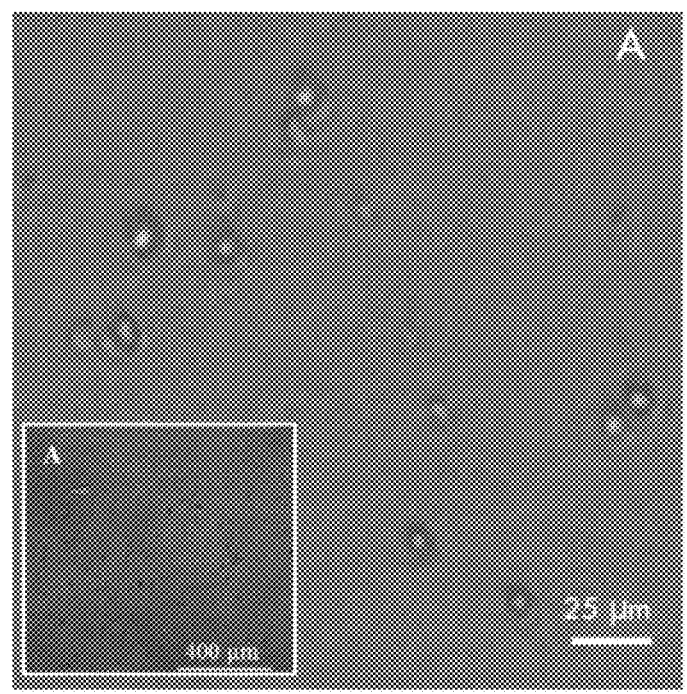
Figure 11B:
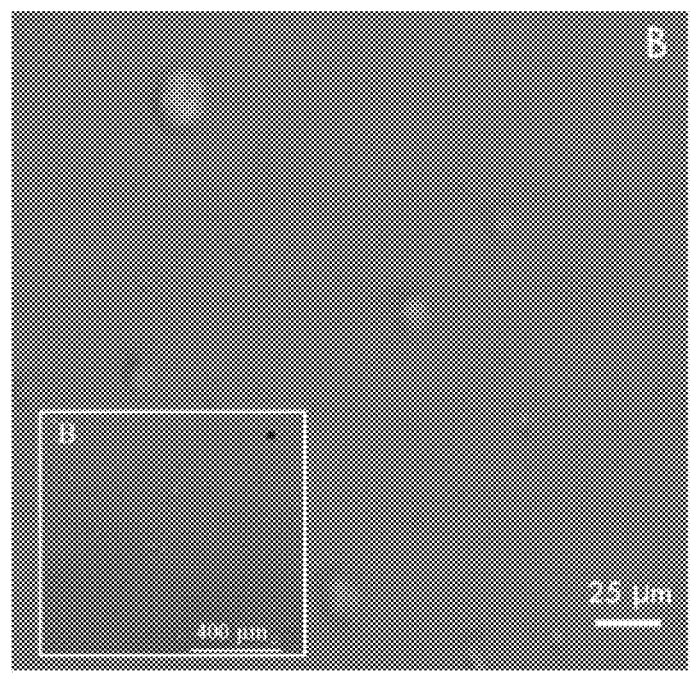

Results:

Dynamic Light Scattering are shown in FIGS. 11A-11B showing the pure PLFA particles having a negative surface charge and Chitosan having a positive surface charge. FIG. 10A shows size distribution and FIG. 10B shows zeta potential. The results show size distribution of example particles synthesized with different addition sequences. DLS gives a distribution of approximately 1500 nm for the composite and 500 nm for pure PLGA; the surface charge is −28 mV for PLGA and +30 mV for the composite and demonstrating the presence of chitosan on the surface. These values are reported for synthesis with 10% (w/v) of PLGA and 3% (w/v) of chitosan.

Qualitative Distribution of a Chitosan:

PLGA-Chitosan composite was synthesized with the fluorescently tagged chitosan to validate its distribution on the composite. It can be seen in inset A of FIG. 11A that chitosan has formed a film on PLGA particles while in inset B of FIG. 11B shows chitosan-PLGA may have formed an interlinked structure or we may have a complete coverage of PLGA. These figures show the chitosan distribution in composite particles. In Sample A Chitosan was added to the PLGA oil-in-water emulsion after 2 hours of solvent evaporation, whereas in Sample B PLGA and chitosan were mixed together and then the volatile solvent was evaporated. By altering the sequence of PLGA and chitosan addition, the distribution of chitosan in the composite particle can be changed; this can be used to control the release profile of the vaccine from the composite.

Total encapsulation of adenovirus is shown in Table 3.

TABLE 3

Adenovirus encapsulated

| Experiment # | % PVA (w/v) | % PLGA (w/v) | % Chitosan Conc (w/v) | Adenovirus soultion (µl) | Total viral particles/mg of particles |
|---|---|---|---|---|---|
| 1 | 3 | 10 | 1 | 400 | 6.5E+06 |
| 2 | 3 | 10 | 3 | 400 | 6.8E+06 |
| 3 | 3 | 10 | 3 | 0 |  |
| 4 | 1 | 10 | 3 | 400 | 2.1E+06 |
| 6 | 3 | 10 | 3 | 0 | 3.1E+07 |
| 7 | 3 | 10 | 0 | 400 | 1.0E+07 |
| 9 | 3 | 10 | 0 | 0 | 1.0E+08 |

* Experiments 1-4: PLGA and chitosan added together; 6-7: PLGA then chitosan added after 2 hours; 9: PLGA only control Example 6

Phase II Comparison of Unencapsulated and Encapsulated Vaccines to test (1) safety, local reactions or systemic toxicity; (2) immunogenicity of encapsulated vaccine which has a primary and boost function; (3) short term durability for 90 and 120 days. Unencapsulated Ad-flu will be administered SQ at minimal responsive dose. The encapsulated vaccine formulation engineered for a delayed release at 5-30 days after immunization will be given as a single dose. The encapsulated doses include: burst release and release delayed for 5-30 days. Mice will be killed at 30 days, to test the pre-boost effects, at 60 days to test the boost response and at 90 and 120 days to test short term durability.

Test Groups Include:

Unimmunized Controls:

Three mice per cohort, including 3 mice killed on Day 0 (that is the day that the immunized are injected) and 3 mice killed on Days 30, 60, 90 and 120 post injection and negative controls for each experimental time point.

Unencapsulated Immunized:

All mice are immunized once SQ on day 0 with minimal responsive dose of $1\times10^6$ IFU/mouse of unencapsulated vaccine as determined in the Phase I Project. Nine (9) mice are included in each cohort and will be killed at 30, 60, 90 and 120 days. The mice are positive controls for immunity of unencapsulated vaccine and compared to the encapsulated formulations for antibody titer and durability of immunity.

Encapsulated Immunized:

All mice will be injected with one of three types of encapsulated vaccine, including particle formulations PLGA alone, Composite Formulation One and Composite Formulation Two. Mice in each experimental group will be injected with $1\times10^6$ IFU/mouse of unencapsulated vaccine as a prime dose and simultaneously injected with a dose of encapsulated vaccine that is projected to release their payload at a time indicated by the in vitro release profile. It is projected that the PLGA only group will release the encapsulated dose within 5-7 days. The Composite groups are designed to release their doses in 30 days. Mice will be killed at 30 days, to test the pre-boost effects, at 60 days to test the boost response and at 90 and 120 days to test short term durability. Sera collected at each time point will be tested for antibody to the vaccine as described below. The injection site and visceral organs were examined for lesions and any suspected abnormalities will be fixed in neutral buffered formalin and processed for microscopic examination and histopathological assessment.

Antibody Assays:

The in vivo antibody response to the vaccine, i.e., immunogenicity, will be assessed using the standard hemagglutinin inhibition (HAI or HI) assay. This assay is routinely performed to evaluate the immunogenicity of influenza vaccines in a variety of animal models as well as humans. It determines the dilution of test serum that is able to block the agglutination of red blood cells by influenza virus. The sample titer is the reciprocal of the highest dilution of serum that allows the red blood cells to form a button at the bottom of the test well (inhibition of agglutination). Standardized reagents and methods are used in the execution of this assay. Alternatively, for samples with low or absent HAI, the serum microneutralization assay can be used to measure antibody against the influenza virus. In this assay, dilutions of test serum are mixed with a fixed amount influenza virus and the mixture is plated on cells permissive for influenza replication. Infection is associated with the presence of cytopathic effect (CPE) and the sample titer is determined as the reciprocal of the highest serum dilution that results in inhibition of CPE. These assays are considered to be standard by the scientific community.

Bioavailability Assays:

Bioavailability is an essential characteristic of nanoencapsulated vaccine that will be tested in vitro. The concentration of vector will be determined using quantitative real-time PCR targeting the boundary of the transgene and the flanking adenoviral sequences. Vector that is either encapsulated in particles or released into surrounding medium will be extracted prior to quantification. Purified vector used during the encapsulation process will serve as calibrator and will also be spiked into the sample prior to extraction to verify extraction efficiency and detect any matrix effects during quantification of the vector. The biological activity of encapsulated and released vector will be determined using a focus forming assay wherein the concentration of biologically active vector particles is assayed by enumerating the number of infected cells 48 hours after series of sample dilutions are inoculated onto permissive cells. Infected cells are identified by the intracellular staining of the adenovirus hexon protein with antibody conjugated to a chromophore or fluorescent moiety. Vector encapsulated in particles will be released/extracted prior determination of the infectious titer. By combining the results of these two analyses, the concentration and activity of the vector encapsulated in particles and released into the medium can be accurately determined and used to express the release rates and stability of the various formulations.

Data Collection and Analysis:

All data collected will identify antigen, dose, signalment of test animal, dates and metrics for antibody titer. Data stored in these cells can be used by either Excel (office.microsoft.com/en-us/excel/) or SAS/STAT statistical analysis software (sas.com/en_us/software/analytics/stat.html) for graphic display and statistical analyses. The experimental design for mouse trials will be cross-sectional sampling of un-vaccinated and vaccinated mouse cohorts at monthly intervals from 30 to 120 days post vaccination. Vaccine dependent effects will be evaluated using the Kruskal-Wallis one-way analysis of Variance and the Dunn's Multiple Comparison Test for means spread. Significance will be set at P<0.05. Based on the recently completed mouse studies, the number of subjects and observations are sufficient to achieve statistical significance.

Example 7

The effect of changing the molar ratio of the polymers and the timing of polymer addition and the adenovirus volume on surface charge and average particle size was further evaluated. As shown below in Table 4, Experiments #1-4 were conducted with PLGA and chitosan polymers mixed together to form the polymers. Experiments #5-8 used PLGA to form an initial particle and then chitosan was added to produce a core-shell type structure. Experiments #9-10 consisted of only PLGA.

Procedure:

For the listed experiments, all particles were freeze dried before starting degradation studies except 7b. All sizes reported are after removing excess of surfactant from the solution except for sample 5 whose size was measured without any excess surfactant removal.

Particles were weighed after freeze drying and 1.2 ml of DMEM culture media was added, to it. These vials were stirred at 37° C. using a rotoflex. After every time point, vials were centrifuged at 5000 rpm for 10 min and the supernatant was collected for the adenovirus released and stored at −80° C. until further use. Fresh 1 ml DMEM culture media was added to vials and further stirred. qPCR was used to quantify the adenovirus collected.

Figure 12A:
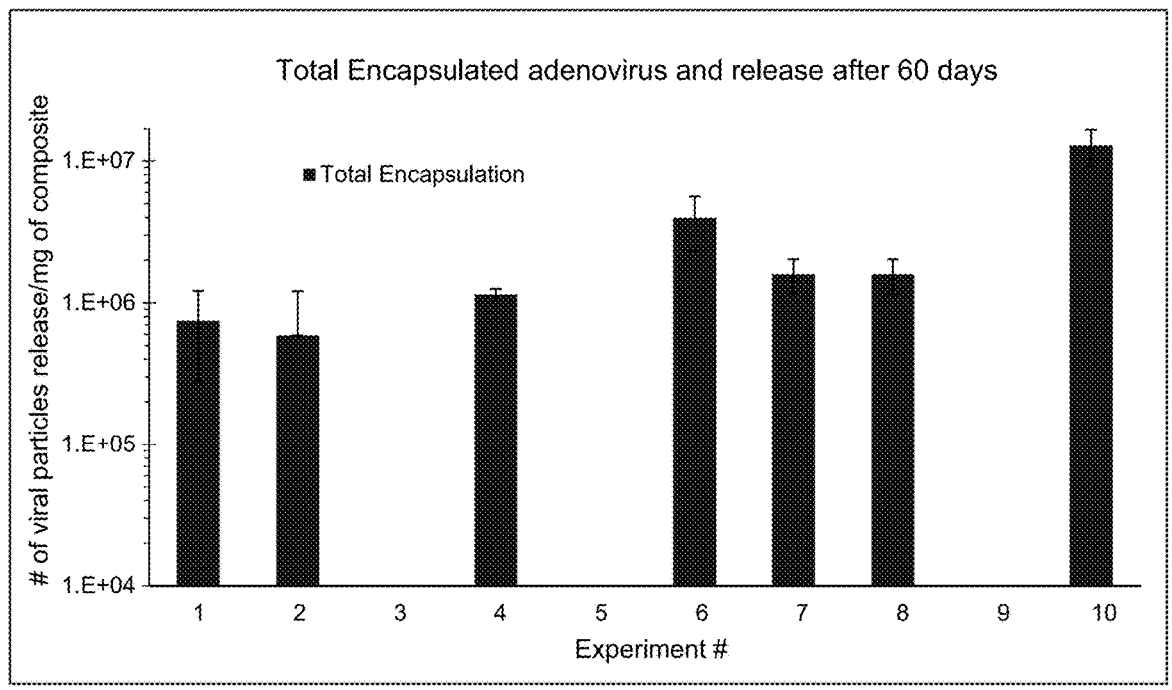
FIGS. 12A-12B show the total adenovirus encapsulated (FIG. 12A) and the amount released in media when sampled over a period of 60 days (FIG. 12B).
Figure 12B:
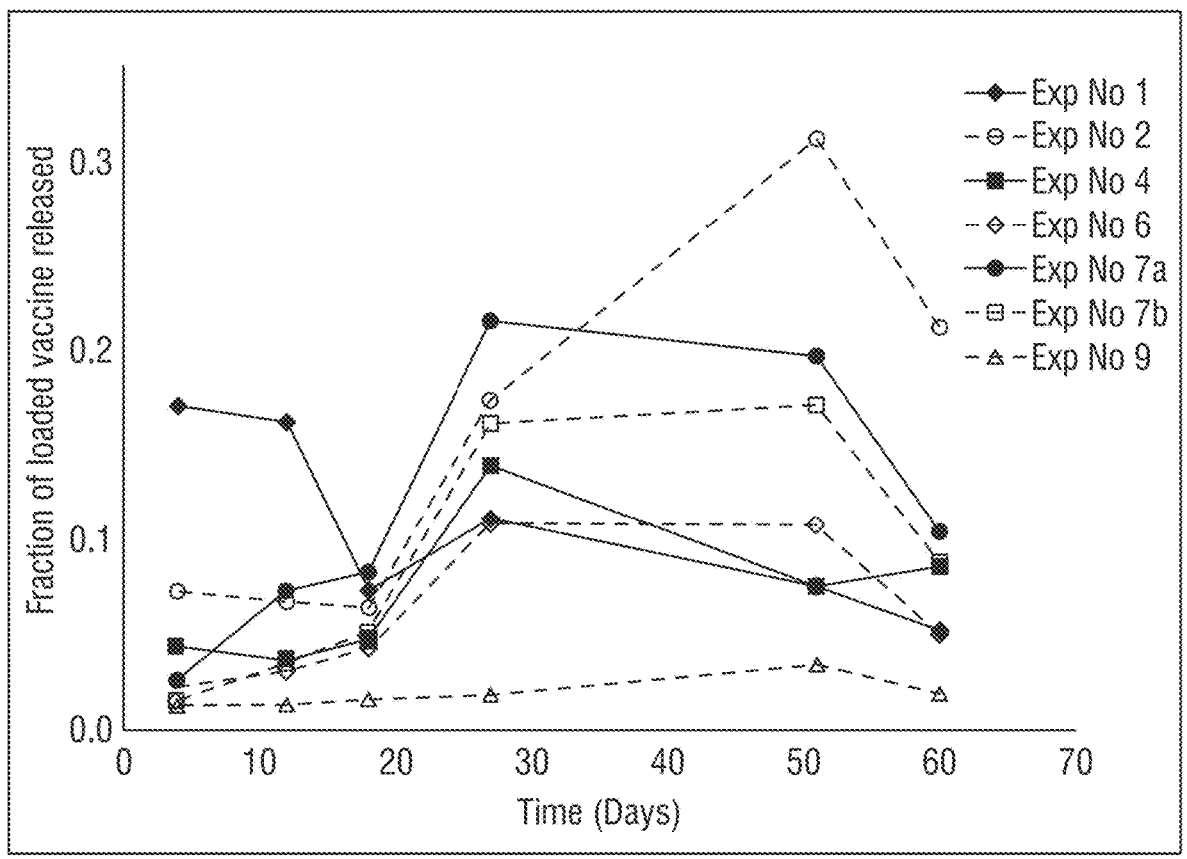

Results: As shown in FIGS. 12A-12B pure PLGA (Exp No 9) has very little adenovirus left for release after a period of about 4 days. The composite particles in this example, however, showed a peak release time between 27 to 50 days from initiation of the in vitro degradation experiments. Among the composites particles, experiment number 7a, which was produced by serial addition of PLGA and then chitosan, showed a high peak of about 22% of loaded vaccine released at day 27. Experiment 2, which was synthesized by simultaneous addition of PLGA and chitosan, showed a peak release at day 50. Particles 7a and 7b have the highest encapsulation efficiency.

The results in Table 4 confirm that surface charge for a particular ratio can vary based on the distribution of polymers (homogenous mixture versus core-shell). In addition, size can be adjusted for any one ratio of polymers.

Example 8

The compositions and pharmaceutical compositions are also suitable for use in delivering vaccines for non-pathogenic antigens. An adenoviral vectored vaccine that is designed to block the function of gonadotropin releasing hormone (GnRH) by expressing the genes for multiple copies of this decapeptide co-expressed with leukotoxins has been formulated according to the invention. Beneficially the vaccine has succeeded in preventing gonadal development in mice. To enhance the use of this vaccine as an immunocontraceptive for population control of domestic, feral and wild animals, the vectored anti-GnRH vaccine was incorporated in the polymers described herein to achieve a single dose delivery sufficient to circulate antibodies that will block GnRH and sustain this immune response.

The inventions being thus described, it will be obvious that the same may be varied in many ways. Such variations are not to be regarded as a departure from the spirit and scope of the inventions and all such modifications are intended to be included within the scope of the following claims.

The above specification provides a description of the manufacture and use of the disclosed compositions and methods. Since many embodiments can be made without departing from the spirit and scope of the invention, the invention resides in the claims.

TABLE 4

| | Factors (3 factors with 2 levels) | | | | | | |
|---|---|---|---|---|---|---|---|
| Experiment No | % PVA (w/v) | % PLGA (w/v) | % Chitosan Conc (w/v) | Adenovirus (µl) | Average Size (nm) | Polydispersity index (PDI) | Zeta potential (mV) |
| 1 | 3 | 10 | 1 | 400 | 2968 | 0.15 | 24.9 |
| 2 | 3 | 10 | 3 | 400 | 2265 | 0.48 | 25.1 |
| 3 | 3 | 10 | 3 | 0 | 3873 | 0.26 | 45.0 |
| 4 | 1 | 10 | 3 | 400 | 2100 | 0.27 | 46.8 |
| 5 | 3 | 1 | 3 | 400 | 3037* | 0.86 | |
| 6 | 3 | 10 | 1 | 400 | 759 | 0.43 | 5.7 |
| 7a | 3 | 10 | 3 | 400 | 771 | 0.33 | 10.1 |
| 7b | 3 | 10 | 3 | 400 | | | |
| 8 | 3 | 10 | 3 | 0 | 1290 | 0.29 | 22.3 |
| 9 | 3 | 10 | 0 | 400 | 375 | 0.25 | 0.9 |
| 10 | 3 | 10 | 0 | 0 | 483 | 0.31 | 0.5 |

What is claimed is:

1. A pharmaceutical composition comprising:
   a) a biodegradable polymeric composite particle comprising: at least one active agent encapsulated in a hollow or aqueous core by a shell comprising a mixture of from about 50 wt-% to about 99 wt-% of a first polymer, wherein the first polymer is a hydrophobic polymer, and from about 1 wt-% to about 50 wt-% of a second polymer comprising chitosan, alginate, or collagen, wherein the first and second polymer are distributed in a gradient from the core to a surface of the composite with the first polymer having a higher concentration at the core and the second polymer having a higher concentration at the surface of the composite; wherein the at least one active agent is released as a delayed dose after a period of at least 7 days to 6 months; and b) at least one additional active agent free from and not encapsulated by the polymeric composite particle; wherein the at least one additional active agent provides an initial burst dose and the polymeric composite particle provides the delayed dose of the at least one active agent, wherein the at least one active agent encapsulated in the core and the at least one additional active agent free from the particle is the same active agent or different active agents; and wherein the polymeric composite particle has a particle size of from about 10 nanometers to less than 900 nanometers.

2. The composition of claim 1, wherein the polymeric composite particle comprises the chitosan or collagen and does not comprise alginate.

3. The composition of claim 1, wherein the polymeric composite particle does not comprise divalent or trivalent cations as cross-linking reagents.

4. The composition of claim 1, wherein the polymeric composite particle does not comprise divalent cations, selected from $Ca^{2+}$, $Sr^{2+}$, $Zn^{2+}$, $Co^{2+}$ or $Ba^{2+}$, or trivalent cations $Fe^{3+}$ or $Al^{3+}$.

5. The composition of claim 1, in a lyophilized or freeze-dried form.

6. The composition of claim 1, wherein the pharmaceutical composition can be provided in a liquid suspension, emulsion and/or lyophilized form.

7. The composition of claim 5, wherein the composition is reconstituted in an aqueous solution, wherein the aqueous solution comprises a pharmaceutical acceptable excipient, diluent, or carrier.

8. The composition of claim 1, wherein the at least one active agent encapsulated in the core and/or the at least one additional active agent free from the particle is a vaccine, a therapeutic agent, an immune mediator, a probiotic, a pharmaceutical, a vitamin, an adjuvant, or a cancer antigen.

9. The composition of claim 1, wherein the polymeric composite particles further comprise an enzyme or catalytic agent.

10. The composition of claim 1, wherein the second polymer is degraded via hydrolysis, enzymatic or catalytic activity, or a combination thereof.

11. The composition of claim 1, wherein the first polymer of the polymeric composite particle is poly (L-glycolic acid) (PLGA), polyglycolic acid (PGA), polylactic acid (PLA), poly(L-lactic acid) (PLLA), polyglycolide, poly-L-lactide, poly-D-lactide, poly(amino acids), polydioxanone, polycaprolactone, polygluconate, polylactic acid-polyethylene oxide copolymers, polyorthoesters, polyhydroxybutyrate, polyanhydride, polyphosphoester, poly(alpha-hydroxy acid), and the second polymer of the polymeric composite particle further comprises dextran, polyester, cellulose, carboxymethyl cellulose, modified cellulose, collagen, DNA, RNA or poly(amino acids).

12. A method for delivering an initial burst dose and a delayed dose in a single administration dose, comprising: administering the pharmaceutical composition of claim 1 to an animal in need thereof.

13. The method of claim 12, further comprising reconstituting a lyophilized form of the pharmaceutical composition prior to administration.

14. The method of claim 12, wherein administration is selected from oral, intranasal, topical, intramuscular, mucosal, intravenous, or intraperitoneal.

15. The method of claim 12, wherein the animal is selected from a human, a horse, a dog, a cat, a pig, a cow, a sheep, a chicken, and a goat.

16. The method of claim 12, wherein the at least one active agent encapsulated in the core and/or the at least one additional active agent free from the particle is a vaccine to an infectious pathogen and the initial burst dose is a prime dose and the delayed dose is a boost dose.

17. The method of claim 16, wherein the delayed dose is delivered as a burst or bolus dose between 2 weeks and 6 months after administration of the pharmaceutical composition.

18. The method of claim 16, wherein the single administration dose induces a rapid and prolonged immune response to the infectious pathogen.

19. The method of claim 18, wherein the infectious pathogen is a virus, bacterium, or fungus.

* * * * *